United States Patent
Gavin et al.

(10) Patent No.: US 9,168,216 B2
(45) Date of Patent: Oct. 27, 2015

(54) CARRIER COMPRISING ONE OR MORE DI AND/OR MONO-(ELECTRON TRANSFER AGENT) PHOSPHATE DERIVATIVES OR COMPLEXES THEREOF

(75) Inventors: Paul Gavin, Chadstone (AU); Robert Gianello, Olinda (AU); Esra Ogru, Wheelers Hill (AU)

(73) Assignee: Vital Health Sciences Pty. Ltd., Melbourne (AU)

( * ) Notice: Subject to any disclaimer, the term of this patent is extended or adjusted under 35 U.S.C. 154(b) by 785 days.

(21) Appl. No.: 11/917,831

(22) PCT Filed: Jun. 16, 2006

(86) PCT No.: PCT/AU2006/000839
§ 371 (c)(1),
(2), (4) Date: Jul. 8, 2008

(87) PCT Pub. No.: WO2006/133506
PCT Pub. Date: Dec. 21, 2006

(65) Prior Publication Data
US 2009/0036354 A1     Feb. 5, 2009

(30) Foreign Application Priority Data

Jun. 17, 2005  (AU) ................................ 2005903198
Aug. 30, 2005  (AU) ................................ 2005904737
May 19, 2006  (AU) ................................ 2006902726

(51) Int. Cl.
*A61K 9/00*       (2006.01)
*A61K 8/67*       (2006.01)
(Continued)

(52) U.S. Cl.
CPC . *A61K 8/678* (2013.01); *A61K 8/34* (2013.01); *A61K 8/355* (2013.01); *A61K 8/55* (2013.01); *A61K 9/0014* (2013.01); *A61K 9/5123* (2013.01); *A61K 31/683* (2013.01); *A61K 47/10* (2013.01); *A61K 47/24* (2013.01);
(Continued)

(58) Field of Classification Search
CPC .................................................. A61K 9/1273
See application file for complete search history.

(56) References Cited

U.S. PATENT DOCUMENTS 2,407,823 A   9/1946  Fieser
2,457,932 A   1/1949  Solmssen et al.
(Continued)

FOREIGN PATENT DOCUMENTS

CA   1337992   1/1996
CA   2426852   5/2002
(Continued)

OTHER PUBLICATIONS

Advantages of Liposomal Delivery Systems for Anthracyclines, Semin. Oncol., 2004, 6 Suppl 13, 5-15.*
(Continued)

*Primary Examiner* — Paul Dickinson
(74) *Attorney, Agent, or Firm* — Michael Best & Friedrich LLP

(57) ABSTRACT

The invention relates to a carrier for administering biologically active compounds comprising one or more $C_1$-$C_4$ alcohols, polyols and polymers thereof, water and one or more di and/or mono-(electron transfer agent) phosphate derivatives or complexes thereof. The carrier may be used in administering biologically active compounds, in particular pharmaceuticals including cosmetic agents.

56 Claims, 4 Drawing Sheets

(51) Int. Cl.

| | |
|---|---|
| A61K 8/34 | (2006.01) |
| A61K 8/35 | (2006.01) |
| A61K 8/55 | (2006.01) |
| A61K 9/51 | (2006.01) |
| A61K 31/683 | (2006.01) |
| A61K 47/10 | (2006.01) |
| A61K 47/24 | (2006.01) |
| A61Q 19/00 | (2006.01) |
| A61K 9/127 | (2006.01) |
| A61Q 19/08 | (2006.01) |

(52) U.S. Cl.
CPC .............. *A61Q 19/00* (2013.01); *A61K 9/1273* (2013.01); *A61Q 19/08* (2013.01)

(56) References Cited

U.S. PATENT DOCUMENTS

| | | | |
|---|---|---|---|
| 2,667,479 A | 1/1954 | Hoffman et al. | |
| 2,913,477 A | 11/1959 | Hirschmann | |
| 3,127,434 A | 3/1964 | Andrews | |
| 3,212,901 A | 10/1965 | Robeson | |
| 3,607,765 A | 9/1971 | Wixon | |
| 4,075,333 A | 2/1978 | Josse | |
| 4,141,938 A | 2/1979 | Klose | |
| 4,299,906 A | 11/1981 | Liu | |
| 4,369,172 A | 1/1983 | Schor et al. | |
| 4,444,755 A | 4/1984 | Horrobin | |
| 4,603,142 A | 7/1986 | Burger et al. | |
| 4,654,373 A | 3/1987 | Bertelli | |
| 4,684,520 A | 8/1987 | Bertelli | |
| 4,686,211 A | 8/1987 | Hara et al. | |
| 4,874,883 A | 10/1989 | Uphues et al. | |
| 4,952,495 A | 8/1990 | Belly et al. | |
| 4,977,282 A | 12/1990 | Baldwin et al. | |
| 5,041,434 A | 8/1991 | Lubkin | |
| 5,053,222 A | 10/1991 | Takasu et al. | |
| 5,091,848 A | 2/1992 | Kojima | |
| 5,094,848 A | 3/1992 | Brixner | |
| 5,114,957 A | 5/1992 | Hendler et al. | |
| 5,138,084 A | 8/1992 | Casagrande et al. | |
| 5,173,304 A | 12/1992 | Lohner et al. | |
| 5,334,378 A | 8/1994 | Mitani et al. | |
| 5,374,645 A | 12/1994 | Kurihara-Bergstrom et al. | |
| 5,387,579 A * | 2/1995 | Meybeck et al. | 514/100 |
| 5,446,070 A | 8/1995 | Mantelle | |
| 5,474,891 A | 12/1995 | Murphy | |
| 5,474,991 A | 12/1995 | Ogata et al. | |
| 5,554,781 A | 9/1996 | Reierson | |
| 5,570,504 A | 11/1996 | DiStefano et al. | |
| 5,583,105 A | 12/1996 | Kovacs et al. | |
| 5,589,504 A | 12/1996 | Dannenberg et al. | |
| 5,603,949 A | 2/1997 | Meybeck et al. | |
| 5,607,921 A | 3/1997 | Bernard et al. | |
| 5,643,597 A | 7/1997 | Meybeck et al. | |
| 5,656,618 A | 8/1997 | Meybeck et al. | |
| 5,656,672 A | 8/1997 | Collin et al. | |
| 5,741,518 A | 4/1998 | Ribier et al. | |
| 5,759,526 A | 6/1998 | Simonnet et al. | |
| 5,776,915 A | 7/1998 | Peterson et al. | |
| 5,780,504 A | 7/1998 | Ptchelintsev | |
| 5,804,168 A | 9/1998 | Murad | |
| 5,804,216 A | 9/1998 | Terren et al. | |
| 5,807,542 A | 9/1998 | Challis et al. | |
| 5,807,845 A | 9/1998 | Ogata et al. | |
| 5,885,595 A | 3/1999 | Corey et al. | |
| 5,906,811 A | 5/1999 | Hersh | |
| 5,908,846 A | 6/1999 | Bundgaard et al. | |
| 5,916,915 A | 6/1999 | Hong et al. | |
| 5,928,631 A | 7/1999 | Lucas et al. | |
| 5,952,361 A | 9/1999 | Dias Nahoum | |
| 5,952,373 A | 9/1999 | Lanzendorfer et al. | |
| 5,965,750 A | 10/1999 | Oonishi et al. | |
| 5,981,474 A | 11/1999 | Manning et al. | |
| 5,985,856 A | 11/1999 | Stella et al. | |
| 6,022,867 A | 2/2000 | Ito et al. | |
| 6,028,105 A | 2/2000 | Nigra | |
| 6,046,181 A | 4/2000 | Oonishi et al. | |
| 6,048,891 A | 4/2000 | Wechter | |
| 6,096,326 A | 8/2000 | Wikholm | |
| 6,121,249 A | 9/2000 | Weissman et al. | |
| 6,143,770 A | 11/2000 | Lane et al. | |
| 6,184,247 B1 | 2/2001 | Schneider | |
| 6,231,885 B1 | 5/2001 | Carrara | |
| 6,248,758 B1 | 6/2001 | Klokkers et al. | |
| 6,248,779 B1 | 6/2001 | Shimizu et al. | |
| 6,361,800 B1 | 3/2002 | Cooper et al. | |
| 6,384,043 B1 | 5/2002 | Peyman et al. | |
| 6,403,811 B1 | 6/2002 | West | |
| 6,417,223 B1 | 7/2002 | Sanders et al. | |
| 6,423,742 B1 | 7/2002 | Larson | |
| 6,444,220 B2 | 9/2002 | Wiley | |
| 6,444,234 B1 | 9/2002 | Kirby et al. | |
| 6,479,540 B1 | 11/2002 | Constantinides et al. | |
| 6,485,950 B1 * | 11/2002 | Kumar et al. | 435/189 |
| 6,503,545 B1 | 1/2003 | Perlman et al. | |
| 6,579,995 B1 | 6/2003 | West | |
| 6,599,933 B2 | 7/2003 | Takata et al. | |
| 6,641,847 B1 | 11/2003 | Nawar | |
| 6,645,998 B2 | 11/2003 | Sanders et al. | |
| 6,703,384 B2 | 3/2004 | Sanders et al. | |
| 6,727,280 B2 | 4/2004 | Palepu et al. | |
| 6,770,672 B1 | 8/2004 | Sanders et al. | |
| 6,887,648 B2 | 5/2005 | Pavelchek et al. | |
| 7,074,825 B2 | 7/2006 | Mo et al. | |
| 7,179,486 B1 | 2/2007 | Mulye | |
| 2001/0006659 A1 | 7/2001 | Koike et al. | |
| 2001/0044462 A1 | 11/2001 | Hensley et al. | |
| 2001/0055602 A1 | 12/2001 | Wiley | |
| 2002/0045765 A1 | 4/2002 | Kim et al. | |
| 2002/0127198 A1 | 9/2002 | Rothbard et al. | |
| 2002/0131994 A1 | 9/2002 | Schur | |
| 2002/0132845 A1 | 9/2002 | Miller et al. | |
| 2002/0151467 A1 | 10/2002 | Leung | |
| 2003/0035812 A1 | 2/2003 | Ito et al. | |
| 2003/0109575 A1 | 6/2003 | Lambert et al. | |
| 2003/0157326 A1 | 8/2003 | Vaghefi et al. | |
| 2003/0206972 A1 | 11/2003 | Babish et al. | |
| 2003/0220301 A1 | 11/2003 | Lal et al. | |
| 2004/0052745 A1 | 3/2004 | Bernard et al. | |
| 2004/0052754 A1 * | 3/2004 | West et al. | 424/70.23 |
| 2004/0067890 A1 | 4/2004 | Gupta | |
| 2004/0096493 A1 * | 5/2004 | West | 424/450 |
| 2004/0097431 A1 | 5/2004 | Sanders et al. | |
| 2004/0097472 A1 | 5/2004 | West et al. | |
| 2004/0102385 A1 | 5/2004 | Ames et al. | |
| 2004/0131569 A1 | 7/2004 | Schneider et al. | |
| 2004/0167081 A1 | 8/2004 | Abbruzzese et al. | |
| 2004/0204343 A1 | 10/2004 | Fishman | |
| 2004/0234602 A1 | 11/2004 | Fischer et al. | |
| 2004/0235938 A1 | 11/2004 | Sanders et al. | |
| 2004/0241225 A1 | 12/2004 | West | |
| 2004/0253318 A1 | 12/2004 | West et al. | |
| 2005/0009787 A1 | 1/2005 | West et al. | |
| 2005/0089495 A1 | 4/2005 | West | |
| 2005/0134664 A1 | 6/2005 | Pavlin | |
| 2005/0220733 A1 | 10/2005 | Tsuzuki et al. | |
| 2006/0120979 A1 | 6/2006 | Rubin | |
| 2006/0228395 A1 | 10/2006 | Lamb et al. | |
| 2006/0241085 A1 | 10/2006 | West et al. | |
| 2006/0257459 A1 | 11/2006 | West et al. | |
| 2006/0281715 A1 | 12/2006 | West | |
| 2006/0281716 A1 | 12/2006 | West et al. | |
| 2007/0042999 A1 | 2/2007 | West et al. | |
| 2007/0135390 A1 | 6/2007 | West et al. | |
| 2007/0141133 A1 | 6/2007 | Wang et al. | |
| 2008/0233178 A1 | 9/2008 | Reidenberg et al. | |
| 2008/0254073 A1 | 10/2008 | Chi | |
| 2009/0004166 A1 | 1/2009 | West et al. | |
| 2009/0005348 A1 | 1/2009 | Ogru et al. | |
| 2009/0104258 A1 | 4/2009 | Dumas et al. | |
| 2009/0186856 A1 | 7/2009 | West et al. | |
| 2009/0233881 A1 | 9/2009 | West et al. | |
| 2009/0239827 A1 | 9/2009 | Ogru et al. | |

(56) References Cited

U.S. PATENT DOCUMENTS

| | | | |
|---|---|---|---|
| 2009/0274677 A1 | 11/2009 | Isaacs et al. | |
| 2010/0076094 A1 | 3/2010 | West | |
| 2010/0209459 A1 | 8/2010 | West et al. | |
| 2010/0222305 A1 | 9/2010 | West et al. | |
| 2010/0261670 A1 | 10/2010 | West et al. | |
| 2011/0003774 A1 | 1/2011 | West et al. | |
| 2014/0255509 A1 | 9/2014 | Libinaki et al. | |

FOREIGN PATENT DOCUMENTS

| | | |
|---|---|---|
| CA | 2426885 | 5/2002 |
| CN | 1600297 | 3/2005 |
| EP | 0171009 | 2/1986 |
| EP | 0324387 | 7/1989 |
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0612521 | 8/1994 |
| EP | 0617963 | 10/1994 |
| EP | 0641790 | 3/1995 |
| EP | 0643969 | 3/1995 |
| EP | 0650721 | 5/1995 |
| EP | 0661053 | 7/1995 |
| EP | 0669132 | 8/1995 |
| EP | 0669437 | 8/1995 |
| EP | 0674904 | 10/1995 |
| EP | 0679399 | 11/1995 |
| EP | 0680760 | 11/1995 |
| EP | 0681840 | 11/1995 |
| EP | 0684043 | 12/1995 |
| EP | 0699440 | 3/1996 |
| EP | 679399 B1 | 8/1997 |
| EP | 0826365 | 3/1998 |
| EP | 0845216 | 6/1998 |
| EP | 0699437 | 12/1998 |
| EP | 0965328 | 12/1999 |
| EP | 1000541 | 5/2000 |
| EP | 1023897 | 8/2000 |
| EP | 1053749 | 11/2000 |
| EP | 1264595 | 12/2002 |
| EP | 1470817 | 10/2004 |
| EP | 1783209 | 5/2007 |
| FR | 2777179 | 10/1999 |
| GB | 778142 | 7/1957 |
| GB | 1121683 | 7/1968 |
| GB | 2227662 | 8/1990 |
| JP | 50-022535 | 3/1975 |
| JP | 52-039013 | 3/1977 |
| JP | 53015381 | 2/1978 |
| JP | 58180410 | 10/1983 |
| JP | 59044375 | 3/1984 |
| JP | 59157091 | 9/1984 |
| JP | 60197621 | 10/1985 |
| JP | 61086940 | 5/1986 |
| JP | 61091137 | 5/1986 |
| JP | 61176535 | 8/1986 |
| JP | 61233631 | 10/1986 |
| JP | 62195393 | 8/1987 |
| JP | 63-093791 | 4/1988 |
| JP | 63139972 | 6/1988 |
| JP | 1228920 | 9/1989 |
| JP | 1274830 | 11/1989 |
| JP | 03-072426 | 3/1991 |
| JP | 03-120230 | 5/1991 |
| JP | 4208209 | 7/1992 |
| JP | 4270212 | 9/1992 |
| JP | 05-000946 | 1/1993 |
| JP | 5132700 | 5/1993 |
| JP | 5201858 | 8/1993 |
| JP | 5509296 | 12/1993 |
| JP | 6048962 | 2/1994 |
| JP | 6056699 | 3/1994 |
| JP | 6502422 | 3/1994 |
| JP | 6078214 | 10/1994 |
| JP | 6508820 | 10/1994 |
| JP | 7011291 | 1/1995 |
| JP | 7207298 | 8/1995 |
| JP | 7507318 | 8/1995 |
| JP | 7278587 | 10/1995 |
| JP | 7316170 | 12/1995 |
| JP | 8073338 | 3/1996 |
| JP | 8193089 | 7/1996 |
| JP | 08-231564 | 9/1996 |
| JP | 8311085 | 11/1996 |
| JP | 8311489 | 11/1996 |
| JP | 8325594 | 12/1996 |
| JP | 9044375 | 2/1997 |
| JP | 9309813 | 12/1997 |
| JP | 10045783 | 2/1998 |
| JP | 10155429 | 6/1998 |
| JP | 10509451 | 9/1998 |
| JP | 10511677 | 11/1998 |
| JP | 11043436 | 2/1999 |
| JP | 11506419 | 6/1999 |
| JP | 11199424 | 7/1999 |
| JP | 11199465 | 7/1999 |
| JP | 2000507557 | 6/2000 |
| JP | 2000198701 | 7/2000 |
| JP | 2001169731 | 6/2001 |
| JP | 2001247585 | 9/2001 |
| JP | 2002080475 | 3/2002 |
| JP | 2002088091 | 3/2002 |
| JP | 2003128531 | 5/2003 |
| JP | 2003171313 | 6/2003 |
| NZ | 244549 | 7/1994 |
| RU | 2296743 | 4/2007 |
| RU | 2302857 | 7/2007 |
| RU | 2373957 | 11/2009 |
| SU | 925961 | 5/1982 |
| UA | 29476 | 11/2000 |
| WO | WO 91/17987 | 11/1991 |
| WO | WO 92/03122 | 3/1992 |
| WO | WO 92/07544 | 5/1992 |
| WO | WO 92/08459 | 5/1992 |
| WO | WO 92/15289 | 9/1992 |
| WO | WO 93/02661 | 2/1993 |
| WO | 93/09768 | 5/1993 |
| WO | WO 93/15731 | 8/1993 |
| WO | WO 93/24131 | 12/1993 |
| WO | WO 95/31217 | 11/1995 |
| WO | WO 95/34303 | 12/1995 |
| WO | WO 96/17852 | 6/1996 |
| WO | WO 96/20715 | 7/1996 |
| WO | WO 96/21440 | 7/1996 |
| WO | WO 96/29336 | 9/1996 |
| WO | 96/37196 | 11/1996 |
| WO | 97/02803 | 1/1997 |
| WO | WO 97/14705 | 4/1997 |
| WO | WO 97/35591 | 10/1997 |
| WO | 99/35242 | 7/1999 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | 00/44237 | 8/2000 |
| WO | 00/44375 | 8/2000 |
| WO | WO 00/53728 | 9/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | 00/74684 | 12/2000 |
| WO | 01/13901 | 3/2001 |
| WO | WO 01/19372 | 3/2001 |
| WO | WO 01/22937 | 4/2001 |
| WO | 01/35883 | 5/2001 |
| WO | WO 01/35998 | 5/2001 |
| WO | WO 01/35998 A1 | 5/2001 |

(56) References Cited

FOREIGN PATENT DOCUMENTS

| WO | WO 01/46204 | 6/2001 |
|---|---|---|
| WO | 01/54674 | 8/2001 |
| WO | WO 01/58889 | 8/2001 |
| WO | 01/72300 | 10/2001 |
| WO | WO 02/13810 | 2/2002 |
| WO | WO 02/26238 | 4/2002 |
| WO | WO 02/36736 | 5/2002 |
| WO | WO 02/39996 | 5/2002 |
| WO | WO 02/40033 | 5/2002 |
| WO | WO 02/40033 A1 | 5/2002 |
| WO | WO 02/40034 | 5/2002 |
| WO | WO 02/40034 A1 | 5/2002 |
| WO | WO 03/011303 | 2/2003 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | WO 03/039461 | 5/2003 |
| WO | WO 03/043570 | 5/2003 |
| WO | WO 03/049774 | 6/2003 |
| WO | WO 03/053407 | 7/2003 |
| WO | 03/068209 | 8/2003 |
| WO | 03/097714 | 11/2003 |
| WO | WO 03/101480 | 12/2003 |
| WO | WO 03/101480 A1 | 12/2003 |
| WO | WO 2004/014432 | 2/2004 |
| WO | WO 2004/060315 | 7/2004 |
| WO | WO 2004/060315 A2 | 7/2004 |
| WO | WO 2004/064831 | 8/2004 |
| WO | WO 2004/091636 | 10/2004 |
| WO | WO 2004/092186 | 10/2004 |
| WO | WO 2004/092187 | 10/2004 |
| WO | WO 2005/023282 | 3/2005 |
| WO | WO 2005/023282 A1 | 3/2005 |
| WO | WO 2005/084678 | 9/2005 |
| WO | WO 2006/012692 | 2/2006 |
| WO | WO 2006/092024 | 9/2006 |
| WO | WO 2006/092025 | 9/2006 |
| WO | WO 2006/133506 | 12/2006 |
| WO | WO 2007/070981 | 6/2007 |
| WO | 2008034178 | 3/2008 |
| WO | 2009146443 | 12/2009 |
| WO | 2011/094814 | 8/2011 |

OTHER PUBLICATIONS

Nakayama, S. et al., "Protective effects of a stable, water-soluble vitamin E on photodamage induced by UVB irradiation in cultured mouse skin," Photomedicine and Photobiology (1998) 20:99-100.
United States Patent Office Action for U.S. Appl. No. 10/416,774 dated Dec. 18, 2009 (11 pages).
United States Patent Office Action for U.S. Appl. No. 10/542,511 dated Jan. 12, 2010 (13 pages).
Gann, P.H. et al., "Lower prostate cancer risk in men with elevated plasma lycopene levels: results of a prospective analysis," Cancer Res. (1999) 59(6):1225-1230.
Min, J. et al., "Effect of apoptosis induced by different vitamin E homologous analogues in human hepatoma cells (HepG2)," J. Hygiene Res. China (2003) 32(4):343-345.
Visarius, T. et al., "Inhibition of human prostate cancer cell proliferation: vitamin E and lycopene targeted pathways regulating cell cycle progression," FASEB J. (2004) 18(8):C103.
Suzuki, T. et al., "The solution behavior and the association structure of long-chain monoalkyl phosphates," Chem. Soc. Japan (1986) 633-640, with English abstract.
United States Patent Office Action for U.S. Appl. No. 10/485,196 dated Jan. 25, 2010 (8 pages).
Gianello, R. et al., "Subchronic oral toxicity study of mixed tocopheryl phosphates in rats," Int'l J. Toxicol. (2007) 26:475-490.
Libinaki, R. et al., "Evaluation of the safety of mixed tocopheryl phosphates (MTP)—a formulation of α-tocopheryl phosphate plus α-di-tocopheryl phosphate," Food Chem. Toxicol. (2006) 44(7):916-932.
Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.
Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.
Negis, Y. et al., "Molecular mechanism of alpha-tocopheryl-phospate transport across the cell membrane," Biochem. Biophys. Res. Comm. (2007) 359:348-353.
Negis, Y. et al., "The effect of tocopheryl phosphates on atherosclerosis progression in rabbits fed with a high cholesterol diet," Arch. Biochem. Biophys. (2006) 450:63-66.
Rerek, M.E. et al., "Disodium lauriminodipropionate tocopheryl phosphates: a potent new anti-inflammatory," Cosmetics & Toiletries magazine (2003) 118(7):63-67.
Rezk, B.M. et al., "The extraordinary antioxidant activity of vitamin E phosphate," Biochim. Biophys. Acta (2004) 1683:16-21.
United States Patent Office Action for U.S. Appl. No. 12/212,803 dated Mar. 12, 2010 (13 pages).
United States Patent Office Action for U.S. Appl. No. 10/524,090 dated Mar. 3, 2010 (18 pages).
Cevc, G., Transdermal drug delivery of insulin with ultradeformable carriers, Clin Pharmacokinet. (2003), vol. 42, No. 5, pp. 461-474.
Cevc, G., et al., Ultraflexible vesicles, Transfersomes, have an extremely low pore penetration resistance and transport therapeutic amount of insulin across the intact mammalian skin, Biochim Biophys Acta (1998), vol. 1368, No. 2, pp. 201-215.
Godin, B., Touitou, E., Ethosomes: new prospects in transdermal delivery, Crit Rev Ther Drug Carrier Syst. (2003), vol. 20, No. 1, pp. 63-102.
Guo, J., Transdermal delivery of insulin in mice by using lecithin vesicles as a carrier. Drug Delivery, (2000), vol. 7, No. 2, pp. 113-116.
Karrer, P., Helv. Chim. Acta., (1940), vol. 23, pp. 1137-1138.
King, M. J., et al., Transdermal delivery of insulin from a novel biphasic lipid system in diabetic rats, Diabetes Technol Ther (2002), vol. 4, No. 4, pp. 479-488.
Owens, D. R., et al., Alternative routes of insulin delivery, Diabet. Med. (2003), vol. 20, No. 11, pp. 886-898.
Iimura, N. et al., "Complex formation between cationic surfactants and insoluble drugs," Bull. Chem. Soc. Jpn. (1999) 72:2417-2422.
United States Patent Office Advisory Action for U.S. Appl. No. 10/542,511 dated May 25, 2010 (3 pages).
Imada, I. et al., "Photochemical reaction of ubiquinone. IV. Coenzymatic activity of ubiquinone and related compounds," Chem. Pharm. Bull. (1965) 13:136-142.
United States Patent Office Action for U.S. Appl. No. 10/498,684 dated Jul. 7, 2010 (21 pages).
United States Patent Office Action for U.S. Appl. No. 11/817,453 dated Aug. 2, 2010 (10 pages).
United States Patent Office Action for U.S. Appl. No. 12/158,932 dated Aug. 19, 2010 (15 pages).
Devaraj, S. et la., "Alpha tocopherol decreases CD36 expression in human monocyte-derived macrophages," J. Lipid Res. (2001) 42:521-527.
Ricciarelli, R. et al., "Vitamin E reduces the uptake of oxidized LDL by inhibiting CD36 scavenger receptor expression in cultured aortic smooth muscle cells," Circulation (2000) 102:82-87.
Teupser, D. et al., "Alpha-tocopherol down-regulates scavenger receptor activity in macrophages," Atherosclerosis (1999) 144:109-115.
Gianello, R. et al., "α-tocopheryl phosphate: a novel, natural form of vitamin E," Free Radical Biol. Med. (2005) 39:970-976.
Negis, Y. et al., "On the existence of cellular tocopheryl phosphate, its synthesis, degradation and cellular roles: a hypothesis," IUBMB Life (2005) 57(1):23-25.
Ogru, E. et al., "Vitamin E phosphate: an endogenous form of vitamin E," Medimond S.r.l. (2003) 127-132.
Traber, M.G. et al., "Human plasma vitamin E kinetics demonstrates rapid recycling of plasma RRR-alpha-tocophero," Proc. Natl. Acad. Sci. USA (1994) 91:10005-10008.
United States Office Action for U.S. Appl. No. 09/979,436 dated Sep. 23, 2002 (6 pages).

(56) References Cited

OTHER PUBLICATIONS

United States Office Action for U.S. Appl. No. 10/416,775 dated Nov. 2, 2005 (10 pages).
United States Office Action for U.S. Appl. No. 10/416,775 dated Jun. 12, 2006 (10 pages).
United States Office Action for U.S. Appl. No. 10/416,775 dated Jul. 12, 2007 (11 pages).
United States Office Action for U.S. Appl. No. 10/416,775 dated Dec. 17, 2008 (6 pages).
United States Office Action for U.S. Appl. No. 10/416,774 dated Sep. 6, 2007 (9 pages).
United States Office Action for U.S. Appl. No. 10/416,774 dated Jun. 11, 2008 (15 pages).
United States Office Action for U.S. Appl. No. 10/416,774 dated Feb. 17, 2009 (15 pages).
United States Office Action for U.S. Appl. No. 10/416,774 dated Apr. 15, 2009 (14 pages).
United States Office Action for U.S. Appl. No. 10/462,480 dated Dec. 1, 2006 (10 pages).
United States Office Action for U.S. Appl. No. 10/462,480 dated Nov. 1, 2007 (10 pages).
United States Office Action for U.S. Appl. No. 10/462,480 dated Feb. 20, 2009 (17 pages).
United States Office Action for U.S. Appl. No. 10/485,196 dated May 29, 2008 (23 pages).
United States Office Action for U.S. Appl. No. 10/485,196 dated Jul. 23, 2009 (9 pages).
United States Office Action for U.S. Appl. No. 10/486,142 dated Mar. 18, 2008 (12 pages).
United States Office Action for U.S. Appl. No. 10/487,743 dated Dec. 2, 2005 (22 pages).
United States Office Action for U.S. Appl. No. 10/487,743 dated Jul. 27, 2006 (23 pages).
United States Office Action for U.S. Appl. No. 10/498,684 dated Oct. 2, 2008 (21 pages).
United States Office Action for U.S. Appl. No. 10/498,684 dated Jun. 23, 2009 (19 pages).
United States Office Action for U.S. Appl. No. 10/524,090 dated Mar. 12, 2008 (12 pages).
United States Office Action for U.S. Appl. No. 10/542,511 dated Aug. 8, 2007 (19 pages).
United States Office Action for U.S. Appl. No. 10/542,511 dated Mar. 31, 2008 (20 pages).
United States Office Action for U.S. Appl. No. 10/542,511 dated Feb. 5, 2009 (23 pages).
United States Office Action for U.S. Appl. No. 10/551,200 dated Jan. 28, 2009 (11 pages).
United States Office Action for U.S. Appl. No. 10/551,201 dated Jan. 24, 2008 (6 pages).
United States Office Action for U.S. Appl. No. 10/551,203 dated Dec. 6, 2006 (13 pages).
United States Office Action for U.S. Appl. No. 10/551,203 dated Sep. 7, 2007 (13 pages).
United States Office Action for U.S. Appl. No. 10/551,203 dated Apr. 11, 2008 (11 pages).
United States Office Action for U.S. Appl. No. 10/551,203 dated Dec. 19, 2008 (13 pages).
United States Office Action for U.S. Appl. No. 10/551,203 dated Jul. 21, 2009 (21 pages).
United States Patent Office Action for U.S. Appl. No. 10/485,196 dated Oct. 29, 2010 (13 pages).
Brandt, M., "Steroid hormone biosynthesis," (2002) printed from http://www.rose_hulman.edu/~brandt/Chem430/Steroids.pdf on Nov. 20, 2010 (7 pages).
Jiang, Q. et al., "γ-tocopherol, the major form of vitamin E in the U.S. diet, deserves more attention," Am. J. Clin. Nutri. (2001) 74(6):714-722.
United States Patent Office Action for U.S. Appl. No. 10/524,090 dated Nov. 23, 2010 (19 pages).
United States Patent Office Action for U.S. Appl. No. 11/817,439 dated Nov. 24, 2010 (15 pages).
United States Patent Office Action for U.S. Appl. No. 11/817,453 dated Oct. 9, 2009 (11 pages).
United States Patent Office Action for U.S. Appl. No. 10/462,480 dated Nov. 27, 2009 (9 pages).
Aberg, F. et al., "Distribution and redox state of ubiquinones in rat and human tissues," Arch. Biochem. Biophys. (1992) 295(2):230-234.
Almeida, M.E.M. et al., "Evaluation of soybean oil deodorization distillate for Vitamin E recovery," Arq. Biol. Tecnol. (1994) 37(4):1003-1011.
Barrett, C.W. et al., "The effect of particle size and vehicle on the percutaneous absorption of fluocinolone acetonide," Brit. J. Dermatol. (1965) 77:576-578.
Bikerman, J.J., "Mechanical destruction of young and old foam films," J. Phys. Chem. (1952) 56:164-165.
Blom, J.H. et al., "Reproductive success of female rainbow trout (*Oncorhynchus mykiss*) in response to graded dietary ascorbyl monophosphate levels," Biol. of Reproduction (1995) 52:1073-1080.
Cevc, G. "Transdermal drug delivery of insulin with ultradeformable carriers," Clin. Pharmacokinet. (2003) 42(5):461-474.
Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.
De Wolfe, F.A. et al., "Ligand-binding proteins: their potential for application in systems for controlled delivery and uptake of ligands," Pharmacol. Rev. (2000) 52(2):207-236.
Devaraj, S. et al., "Modulation of monocyte-macrophage function with alpha-tocopherol: implications for atherosclerosis," Nat. Rev. (2002) 60(1):8-14.
Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.
Ernster, L. et al., "Biochemical, physiological and medical aspects of ubiquinone function," Biochim. Biophys. Acta (1995) 1271:195-204.
Octoplus, "Formulation Development of Poorly Soluble Drugs" (www.octoplus.nl) (1999) 2 pages (downloaded Nov. 2008).
Fracalossi, D.M. et al., "Oscars, *Astronotus ocellatus*, have a dietary requirement for vitamin C," J. Nutrition (1998) 128:1745-1751.
Frei, B. et al., "Ubiquinol-10 is an effective lipid-soluble antioxidant at physiological concentrations," Proc. Natl. Acad. Sci. (1990) 87:4879-4883.
Godin, B. et al., "Ethosomes: new prospects in transdermal delivery," Crit. Rev. Thera. Drug Car. Syst. (2003) 20(1):63-102.
Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.
Griffin, E. et al., "A link between diabetes and atherosclerosis: glucose regulates expression of CD36 at the level of translation," Nature Med. (2001) 7(7):840-846.
Guo, J. et al., "Transdermal delivery of insulin in mice by using Lecithin vesicles as a carrier," Drug Del. (2000) 7:113-116.
Heron-Milhavet, L. et al., "Muscle-specific overexpression of CD36 reverses the insulin resistance and diabetes of MKR mice," Endocrinology (2004) 145:4667-4676.
Kagan, V. et al., "Antioxidant effects of ubiquinones in microsomes and mitochondria are mediated by tocopherol recycling," Biochem. Biophys. Res. Commun. (1990) 169(3):851-857.
Karrer, V.P. et al., "d,1-alpha-tocopherol-phosphorsaure-ester," Zurich, Chemisches Institut der Universitat (1933) p. 1137-1138, in German.
King, M.J. et al., "Transdermal delivery of insulin from a novel biphasic lipid system in diabetic rats," Diab. Tech. Therap. (2002) 4(4):479-488.
Knowler, W.C. et al., "Preventing Non-insulin-dependent diabetes," Diabetes (1995) 44:483-488.
Langsjoen, P.H. et al., "Overview of the use of CoQ10 in cardiovascular diseases," Biofactors (1999) 9:273-284.

(56) References Cited

OTHER PUBLICATIONS

Lass, A. et al., "Electron transport-linked ubiquinone-dependent recycling of α-tocopherol inhibits autooxidation of mitochondrial membranes," Arch. Biochem. Biophys. (1998) 352(2):229-236.
Lee, C-F. et al., "Attenuation of UV-induced apoptosis by coenzyme Q10 in human cells harboring large-scale deltion of mitochontrial DNA," Ann. N.Y. Acad. Sci. (2005) 1042:429-438.
Lei, B. et al.,. Progress in alpha-tocopherol preparation technology, Xiandai Huagong (1997) 17(7):13-15.
Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.
Mellors, A. et al., "The inhibition of mitochondrial peroxidation by ubiquinone and ubiquinol," J. Biol. Chem. (1966) 241(19):4353-4356.
Merck Index, The, "α-estradiol" Thirteenth Edition, Whitehouse Station, NJ (2001) p. 660.
Merck Index, The, "Fludarabine to Fludeoxyglucose F18" pages, Thirteenth Edition, Whitehouse Station, NJ (2001) pp. 729-730.
Miyamoto, S. et al., "Synthesis of a novel phosphate ester of a vitamin E derivative and its antioxidative activity," Biosci. Biotech. Biochem. (1998) 62(12):2463-2466.
Morgan, T.M. et al., "Transdermal delivery of estradiol in postmenopausal women with a novel topical aerosol," J. Pharm. Sci. (1998) 87(10):1226-1228.
Morgan, T.M. et al., "Enhanced transdermal delivery of sex hormones in swine with a novel topical aerosol," J. Pharm. Sci. (1998) 87(10):1219-1225.
Mortensen, S.A., "Perspectives on therapy of cardiovascular diseases with coenzyme Q10 (ubiquinone)," Clin. Investig. (1993) 71 (Suppl. 8):S116-S123.
Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.
Ostrenga, J. et al., "Significance of vehicle composition I: Relationship between topical vehicle composition, skin penetrability, and clinical efficacy," J. Pharm. Sci. (1971) 60(8):1175-1179.
Owens, D.R. et al., "Alternative routes of insulin delivery," Diabet. Med. (2003) 20:886-898.
Parker et al., "Neonatal vitamin K administration and childhood cancer in the North of England: retrospective case-control study," BMJ (1998) 316:189-193.
Potts, R.O. et al., "Predicting skin permeability," Pharm. Res. (1992) 9(5):663-669.
Puratchikody, A. et al., "Reverse phase-high performance liquid chromatographic determination of atorvastatin calcium in solid dosage forms," Pharma. Review (2003) 1(2):79-80, 83—STN File CA, Abstract 139:399976 only.
Sevastianov, V.I. et al., "Transdermal delivery of insulin," Meditsinskaia Tekhnika (2003) 2:21-24.
Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.
Singh, R.B. et al., "Randomized double-blind placebo-controlled trial of coenzyme Q10 in patients with acute myocardial infarction," Cardiov. Drugs Ther. (1998) 12:347-353.
Stedman's Medical Dictionary, "Tocopherol," "Tocotrienol," and "Vitamin K1", 22nd Edition, Williams & Wilkins Co. (1972) p. 1303 and 1400.
United States Patent Office Action for U.S. Appl. No. 11/817,439 dated May 11, 2011 (11 pages).
United States Patent Office Action for U.S. Appl. No. 12/628,443 dated Feb. 18, 2011 (15 pages).
United States Patent Office Action for U.S. Appl. No. 12/628,443 dated Aug. 5, 2011 (8 pages).
United States Patent Office Action for U.S. Appl. No. 11/817,439 dated Jul. 29, 2011 (2 pages).
Walters et al., "The effects of surfactants on penetration across the skin" International Journal of Cosmetic Science (1993), vol. 15, pp. 260-270.
Schwenke, D.C. et al., "α-tocopherol protects against diet induced atherosclerosis in New Zealand white rabbits," J. Lipid Res. (2002) 43:1927-1938.
United States Patent Office Notice of Allowance for U.S. Appl. No. 10/485,196 dated Apr. 14, 2011 (7 pages).
United States Patent Office Action for U.S. Appl. No. 12/834,553 dated Apr. 14, 2011 (13 pages).
United States Patent Office Action for U.S. Appl. No. 11/817,453 dated Mar. 9, 2011 (12 pages).
United States Patent Office Action for U.S. Appl. No. 14/086,738 dated May 22, 2014 (14 pages).
United States Patent Office Action for U.S. Appl. No. 13/683,698 dated Jun. 20, 2014 (17 pages).
United States Patent Office Action for U.S. Appl. No. 11/572,864 dated Jun. 20, 2014 (11 pages).
Gavin, P. et al., "Transdermal delivery of various molecules in vivo using alpha-tocopheryl phosphate," Drug Delivery Technology (2008) 8(9):34-41.
United States Patent Office Action for U.S. Appl. No. 11/572,864 dated Sep. 16, 2013 (10 pages).
United States Patent Office Final Rejection for U.S. Appl. No. 13/501,494 dated Aug. 22, 2013 (13 pages).
United States Patent Office Action for U.S. Appl. No. 13/501,499 dated Sep. 25, 2013 (12 pages).
United States Patent Office Final Rejection for U.S. Appl. No. 13/577,124 dated Aug. 2, 2013 (14 pages).
Li et al ("Effect of HPMC and Carbopol on the release and floating properties of gastric floating drug delivery system using factorial design." International Journal of Pharmaceutics, 2003; 253:13-22.).
Barry ("Novel mechanisms and devices to enable successful transdermal drug delivery." Sciences, 2001; 14:101-114).
United States Patent Office Notice of Allowance for U.S. Appl. No. 13/501,500 dated Aug. 21, 2013 (11 pages).
United States Patent Office Notice of Allowance for U.S. Appl. No. 12/628,443 dated Jan. 12, 2012 (7 pages).
United States Patent Office Action for U.S. Appl. No. 13/577,124 dated Feb. 14, 2013 (15 pages).
United States Patent Office Action for U.S. Appl. No. 13/501,498 dated Feb. 21, 2013 (12 pages).
Maugard et al., "Synthesis of Water-Soluble Retinol Derivatives by Enzymatic Method," Biotechnol. Prog., 2002, vol. 18, pp. 424-428.
United States Patent Office Action for U.S. Appl. No. 13/683,698 dated Apr. 24, 2013 (18 pages).
United States Patent Office Action for U.S. Appl. No. 12/782,560 dated May 24, 2012 (22 pages).
United States Patent Office Action for U.S. Appl. No. 12/782,564 dated May 24, 2012 (25 pages).
United States Patent Office Action for U.S. Appl. No. 12/690,735 dated Aug. 2, 2012 (9 pages).
United States Patent Office Action for U.S. Appl. No. 12/782,438 dated Aug. 30, 2012 (14 pages).
United States Patent Office Action for U.S. Appl. No. 11/572,864 dated Nov. 8, 2012 (16 pages).
Sinha, V.R. et al., "Coating polymers for colon specific drug delivery: A comparative in vitro evaluation," Acta. Pharm., 2003, vol. 53, pp. 41-47.
Blum, A. et al., "Clinical and inflammatory effects of dietary L-arginine in patients with intractable angina pectoris," Amer. J. Cardiol. (1999) 1488-1489.
Isoda, K. et al., "Metformin inhibits proinflammatory responses and nuclear factor-κB in human vascular wall cells," Arterioscler. Thromb. Vasc. Biol. (2006) 26:611-617.
United States Patent Office Action for U.S. Appl. No. 11/572,864 dated Mar. 15, 2012 (15 pages).
Japanese Patent Office Action for Application No. 2008-516074 dated Dec. 20, 2011 (5 pages).
United States Patent Office Action for U.S. Appl. No. 12/768,307 dated Oct. 6, 2011 (13 pages).
United States Patent Office Action for U.S. Appl. No. 12/782,564 dated Sep. 1, 2011 (10 pages).

(56) References Cited

OTHER PUBLICATIONS

United States Patent Office Action for U.S. Appl. No. 12/834,553 dated Oct. 7, 2011 (11 pages).
United States Patent Office Action for U.S. Appl. No. 12/690,735 dated Sep. 27, 2011 (15 pages).
United States Patent Office Action for U.S. Appl. No. 11/817,453 dated Oct. 13, 2011 (14 pages).
United States Patent Office Action for U.S. Appl. No. 12/782,560 dated Sep. 1, 2011 (18 pages).
Anslyn, E.V. et al., Modern Physical Organic Chemistry. Chapter 3: Solutions and Non-Covalent Binding Forces. University Science Books. (2006) see p. 146.
Block, L.H., "Chapter 44: Medicated Topicals," in Remington: The Science and Practice of Pharmacy, 20th edition, Edited by Alfonso R. Gennaro, Baltimore, MD, Lippincott, Williams & Wilkins (2000) 836-857.
International Specialty Products,"A Product Guide. Performance enhancing Products for Pharmaceuticals," (2005) 20 pages [retrieved on Jul. 27, 2010 from http://web.archieve.org/web/20060623233652/http://abstracts.aapspharmaceutica.com/ExpoAAPS06/Data/EC/Event/Exhibitors/309/4ecb9a3a-65d0-4c69-a762-c60e099922ee.pdf, published on Jun. 23, 2006 as per Wayback Machine].
Mottu, F. et al., "Organic solvents for pharmaceutical parenterals and embolic liquids: a review of toxicity data," PDA Journal of Pharm. Sci. Tech. (2000) 54(6):456-469.
Williams, A.C. et al., "Penetration enhancers," Advanced Drug Delivery Reviews (2004) 56(5):603-618.
Munteanu et al., "Modulation of cell proliferation and gene expression by -tocopheryl phosphates: relevance to atherosclerosis and inflamation" Biochemical and Biophysical Research Communications, 2004, vol. 318, pp. 311-316.
Rosenson et al., "Hypertriglyceridemia is associated with an elevated blood viscosity Rosenson: triglycerides and blood viscosity", Atherosclerosis, 2002, vol. 161, Issue 2, pp. 433-439.
United States Patent Office Action for U.S. Appl. No. 11/817,453 dated Feb. 21, 2014 (13 pages).
United States Patent Office Action for U.S. Appl. No. 13/501,494 dated Apr. 21, 2014 (19 pages).
Madhavi et al., "Enhanced transdermal drug penetration of curcumin via ethosomes," Malaysian Journal of Pharmaceutical Sciences (2013) 11(1):49-58.
United States Patent Office Final Rejection for U.S. Appl. No. 13/501,498 dated Nov. 14, 2013 (10 pages).
United States Patent Office Final Rejection for U.S. Appl. No. 13/683,698 dated Nov. 14, 2013 (15 pages).
Squillante et al, European Journal of Pharmaceutics and Biopharmaceutics 46 (1998) 265-271.
Guthrie et al., VIIth Asian Conference of Nutrition: Lipid Symposium Proceedings, Journal of Nutrition, 1997, vol. 127, pp. 544s-548s.
Jiang, Q. et al., "γ-tocopherol induces apoptosis in androgen-responsive LNCaP prostate cancer cells via caspase-dependent and independent mechanisms," Annals of the New York Academy of Sciences, 2004, vol. 103, pp. 399-400.
Koh, "Antioxidants in a carotenoid-rich edible oil," Journal of Japan Mibyou System Association, 2003, vol. 9, No. 1, pp. 12-13.
Pastori et al., "Lycopene in association with α-tocopherol inhibits at physiological concentrations proliferation of prostate carcinoma cells," Biochemical and Biophysical Research Communications, 1998, vol. 250, pp. 582-585.
United States Patent Office Action for U.S. Appl. No. 11/817,439 dated Nov. 7, 2012 (10 pages).
United States Patent Office Action for U.S. Appl. No. 13/501,494 dated Dec. 18, 2012 (13 pages).
United States Patent Office Action for U.S. Appl. No. 13/501,500 dated Dec. 17, 2012 (14 pages).
Sharma H. et al., "An excerpt from the medical textbook Contemporary Ayurverda," Edinburgh: Churchill Livingston, 1998, 6 pages, Retrieved from Internet on Nov. 1, 2012 <URL: http://www.bsherman.net/freeradicals.htm>.
United States Patent Office Action for U.S. Appl. No. 13/501,498 dated Nov. 21, 2014 (9 pages).
Zia et al., Pharmaceutical Research, vol. 8, No. 4, 1991.
United States Patent Office Final Rejection for U.S. Appl. No. 13/501,498 dated Apr. 8, 2015 (16 pages).
United States Patent Office Final Rejection for U.S. Appl. No. 13/683,698 dated Jan. 29, 2015 (17 pages).
United States Patent Office Action for U.S. Appl. No. 14/004,973 dated Apr. 9, 2015 (12 pages).
United States Patent Office Action for U.S. Appl. No. 14/550,514 dated Apr. 23, 2015 (13 pages).
Magnusson et al., "Terpenes and ethanol enhance the transdermal permeation of the tripeptide thyrotropin releasing hormone in human epidermis," International Journal of Pharmaceutics 157, 1997, 113-121.
United States Patent Office Action for U.S. Appl. No. 13/501,494 dated Nov. 18, 2014 (16 pages).
United States Patent Office Action for U.S. Appl. No. 13/577,124 dated Dec. 26, 2014 (9 pages).

* cited by examiner

CARRIER COMPRISING ONE OR MORE DI AND/OR MONO-(ELECTRON TRANSFER AGENT) PHOSPHATE DERIVATIVES OR COMPLEXES THEREOF

CROSS-REFERENCE TO RELATED APPLICATIONS

This application is a national stage filing under 35 U.S.C. 371 of International Application No. PCT/AU2006/000839, filed on Jun. 16, 2006, which claims priority to Australian Patent Application No. 2005903198, filed on Jun. 17, 2005, and to Australian Patent Application No. 2005904737, filed on Aug. 30, 2005, and to Australian Patent Application No. 2006902726, filed on May 19, 2006.

FIELD

The invention relates to a carrier for use in administering biologically active compounds and formulations containing biologically active compounds and the carrier. The carrier assists in improving the efficacy, transport and delivery of the biologically active compounds, in particular pharmaceuticals including cosmetic agents.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

The major objective in pharmaceutical delivery is to obtain an appropriate biological effect at a desired site of action. The choice of formulation can be critical to the efficacy of a pharmaceutical since the bioactivity of a pharmaceutical will be sub-optimal if it does not possess the correct physiochemical properties to allow release from the formulation at the target site of action.

Enteral delivery involves administering the pharmaceutical via the GI tract where the pharmaceutical is absorbed and distributed via the bloodstream to the target site of action. For example, pharmaceuticals delivered orally are absorbed through the intestine.

The chemical environment of the GI tract is also important to external pharmaceutical delivery. The pharmaceutical must be in a form which is stable at the different pH of the various parts of the GI tract. If the pharmaceutical forms a non-absorbable complex or is degraded chemically or enzymatically then this will decrease absorption. The pharmaceutical must also be in solution in the GI fluids to be absorbed. Sedimentation of the pharmaceutical involves the pharmaceutical forming solid particles and thus leaving the solution. Adsorption onto luminal solid particles involves solids adsorbing the pharmaceutical; that is, removing the pharmaceutical from solution. Both sedimentation and adsorption decrease absorption of the pharmaceutical. In many cases, degradation and complexation can be circumvented, or at least minimized, by chemical or formulation approaches so that they do not present a limitation to pharmaceutical uptake.

Further, if a pharmaceutical is absorbed through the intestinal or stomach wall, it then must pass through the liver. The liver is designed to eliminate foreign compounds from the body. As a result, a significant proportion of the pharmaceutical (for example, 40-50%) may be metabolised and excreted before its reaches the bloodstream. It is possible to reduce the effect of the liver on enteral administration by having the pharmaceutical absorbed through the lining of the mouth (bucchal/sublingual) or the lining of the rectum (suppositories), however these routes are not always appropriate.

Attempts to improve the bioavailability of enterally administered pharmaceuticals involve either the formation of pro-drugs, for example morphine sulphate or the use of excipients which improve absorption.

Topical delivery involves administering the pharmaceutical to a membrane of the body where the pharmaceutical is absorbed and distributed. For example, pharmaceuticals delivered transdermally are absorbed through the skin.

The skin is the largest organ of the body, which functions to protect the internal organs from external chemical, physical and pathological hazards. Normal skin is divided into three layers: the epidermis, the dermis, and subcutaneous tissue. The outer cornified layer of the epidermis, the stratum corneum, possesses properties of strength, flexibility, high electrical impedance and dryness that retards penetration and proliferation of micro-organisms. The stratum corneum is also the principle barrier to transdermal pharmaceutical absorption. There is a layer of sebum protecting the skin which is considered to be a barrier to all aqueous based pharmaceutical formulations.

When travelling through the skin, a diffusing pharmaceutical molecule has three potential routes of entry to the deeper skin layers: the intercellular route, the transcellular route, and the transappendageal route. While shunt diffusion of electrolytes and large molecules through appendages may be significant, the relatively small area available for transport (0.1% of skin surface) means this route has a negligible contribution to steady state pharmaceutical flux. The main route for the permeation of the majority of molecules is commonly believed to be the intercellular route, and hence many enhancing techniques are aimed at disrupting the strong "brick and mortar" construction of the strata corneum. Current theories regarding the transport route point to two possible mechanisms: (i) passive transcellular and (ii) intracellular epidermal transport.

Pharmaceuticals are topically applied to the skin in a number of ways including ointments, patches, solutions, subcutaneous depots, poultices, plasters and transdermal delivery devices.

Interest in transdermal pharmaceutical delivery may be increasing but some fundamental limitations restrict broader application of the technology. The main limitation to the use of transdermal delivery is the rate of transport of the pharmaceutical through the skin.

Not every pharmaceutical can be administered transdermally at a rate sufficiently high enough to achieve blood levels that are therapeutically beneficial for systemic medication. Pharmaceuticals with similar molecular weights and sizes for example may absorb across the skin at different rates. Fentanyl for example permeates the skin at 2 mg/cm$^2$/hr compared to ephedrine at 200 mg/cm$^2$/hr. The large size of a transdermal delivery system required for fentanyl would therefore be neither practical nor economical despite the advantages of the administration route.

Skin enhancers and various formulation techniques have been developed to improve pharmaceutical absorption through the skin. Skin enhancers can include compounds like capric acid, oleic acid, azone, decylmethyl sulfoxide and hydroxy cinnamates that typically function to modify structure especially of the stratum corneum by dissolving the lipid matrix to improve permeability of pharmaceuticals. Dermal absorption of progesterone for example increases by 143% when the stratum corneum is delipidized. The enhancement increases to 843% when the stratum corneum is totally eliminated. With such aggressive modification, commonly reported problems with repeated use of such systems are therefore evident, including contact dermatitis, reddening of the skin, itching and burning that requires movement of the patch, or application of the pharmaceutical, around the body to prevent local irritation. The reddening is said to disappear within hours of removing the patch. But concern has been raised with respect to long term risk and safety with use of this type of transdermal delivery systems, mainly because increased pharmaceutical permeability is achieved at the cost of damaging a fundamentally important protective layer of the skin.

There is a need for formulations which further improve the bioavailability of biologically active compounds.

SUMMARY

It has been found that the efficacy, transport and delivery of biologically active compounds can be increased if they are administered in a carrier comprising one or more $C_1$-$C_4$ alcohols, polyols and polymers thereof, water and one or more di- and/or mono-(electron transfer agent) phosphate derivatives or complexes thereof.

According to a first aspect of the invention, there is provided a carrier for administering biologically active compounds comprising one or more $C_1$-$C_4$ alcohols, polyols and polymers thereof, water and one or more di- and/or mono-(electron transfer agent) phosphate derivatives or complexes thereof.

The present invention also provides use of one or more $C_1$-$C_4$ alcohols, polyols and polymers thereof, water and one or more di- and/or mono-(electron transfer agent) phosphate derivatives or complexes thereof in the manufacture of a carrier for administering biologically active compounds.

There is also provided a process for the preparation of the carrier defined above which comprises the steps of:
(a) combining one or more di- and/or mono-(electron transfer agent) phosphate derivatives or complexes thereof with one or more $C_{1-4}$ alcohols, polyols or polymers thereof; and
(b) adding water to the combination of step (a).

It will be understood that the carrier may be prepared from or the reaction product of the alcohol, water and electron transfer agent phosphate derivatives or complexes thereof. Under these circumstances, the alcohol, water and electron transfer agent phosphate derivatives or complexes thereof may interact and be present in modified forms.

Preferably, the $C_1$-$C_4$ alcohol is ethanol.

The carrier preferably contains one or more di-(electron transfer agent) phosphate derivatives or a combination of one or more di-(electron transfer agent) phosphate derivatives and one or more mono-(electron transfer agent) phosphate derivatives.

It will be understood that the term "di- and/or mono-(electron transfer agent) phosphate derivative" refers to phosphate esters of electron transfer agents in which the phosphate may be ortho-phosphate or pyro-phosphate di- or mono-substituted with electron transfer agents.

In one embodiment, the di-(electron transfer agent) phosphate derivative is selected from the group consisting of di-tocopheryl phosphate derivatives, di-tocopheryl di-phosphate derivatives, di-tocotrienol phosphate derivatives and mixtures thereof. Preferably, the di-(electron transfer agent) phosphate derivative is di-tocopheryl phosphate.

The mono-(electron transfer agent) phosphate derivative is preferably selected from the group consisting of mono-tocopheryl phosphate derivatives, mono-tocopheryl di-phosphate derivatives, mono-tocotrienyl phosphate and mixtures thereof.

In one preferred embodiment, the formulation is prepared using at least one of di-tocopheryl phosphate, di-tocopheryl di-phosphate and di-tocotrienol phosphate.

In another preferred embodiment, the formulation is prepared using a combination of at least one of mono-tocopheryl phosphate, mono-tocopheryl di-phosphate and mono-tocotrienyl phosphate with at least one of di-tocopheryl phosphate, di-tocopheryl diphosphate and di-tocotrienyl phosphate.

When the formulation contains a combination of mono-tocopheryl phosphate and di-tocopheryl phosphate, these compounds may be present in one or more of their alpha, beta, gamma and delta forms, preferably alpha and gamma forms.

The ratio of mono-tocopheryl phosphate to di-tocopheryl phosphate is preferably 4:1 to 1:4, more preferably 2:1.

The present invention further provides a formulation comprising a biologically active compound and a carrier comprising one or more $C_1$-$C_4$ alcohols, polyols and polymers thereof, water and one or more di- and/or mono-(electron transfer agent) phosphate derivatives or complexes thereof.

The present invention still further provides a method for preparing the formulation defined above comprising the step of combining a biologically active compound with a carrier comprising one or more $C_1$-$C_4$ alcohols, polyols and polymers thereof, water and one or more di- and/or mono-(electron transfer agent) phosphate derivatives or complexes thereof.

Further according to the present invention there is provided a method for administering biologically active compounds which comprises the step of combining the biologically active compound with a carrier comprising one or more $C_1$-$C_4$ alcohols, polyols and polymers thereof, water and one or more di- and/or mono-(electron transfer agent) phosphate derivatives or complexes thereof.

The carrier may be in the form of vesicles. The biologically active compound may be at least partially encapsulated by the vesicles. While not wishing to be bound by theory, it is believed that the formation of vesicles with controlled malleability enables the formulation to traverse intercellular pathways and deliver the biologically active compound intracellularly to target cells or into the systemic circulation. The di- and/or mono-(electron transfer agent) phosphate derivatives assist in countering any inflammation caused by administration of the formulation.

DETAILED DESCRIPTION

The carrier of the present invention contains one or more $C_1$-$C_4$ alcohols, polyols and polymers thereof, water and one or more di- and/or mono-(electron transfer agent) phosphate derivatives or complexes thereof. Preferably, the amount of water present is in the range of 50 to 99%, more preferably 60 to 95%, most preferably 70 to 90%.

The carrier is then combined with a biologically active compound to form a formulation.

Alcohol

The term "$C_1$-$C_4$ alcohol" refers to alcohols having 1 to 4 carbon atoms such as $C_{1-4}$ alkanols, for example, methanol, ethanol, propanol isopropanol or butanol. Polyols and polymers of $C_{1-4}$ alcohols include glycols such as propylene glycol or polyethylene glycol, for example PEG400. Combinations of alcohols may also be used. Ethanol is preferred.

The amount of $C_1$-$C_4$ alcohol present is preferably in the range of 0.5 to 50%, more preferably 5 to 40%, most preferably 10 to 30%.

Electron Transfer Agent Phosphate Derivative

The term "electron transfer agent" refers to an agent which may be phosphorylated and which (in the non-phosphorylated form) can accept an electron to generate a relatively stable molecular radical or accept two electrons to allow the agent to participate in a reversible redox system. Examples of electron transfer agents that may be phosphorylated include hydroxy chromans such as alpha, beta, gamma and delta tocols in enantiomeric and racemic forms; quinols being the reduced forms of electron transfer agent K1 and ubiquinone; hydroxy carotenoids such as retinol; calciferol and ascorbic acid. Preferably, the electron transfer agent is selected from the group consisting of tocols, retinol, quinols being the reduced form of electron transfer agent K1 and mixtures thereof.

More preferably, the electron transfer agent is a tocol such as tocopherol or tocotrienol. The tocols include all isomers of derivatives of 6:hydroxy 2:methyl chroman having the formula (I) below including the α-5:7:8 tri-methyl; β-5:8 di-methyl; γ-7:8 di-methyl; and δ 8 methyl derivatives.

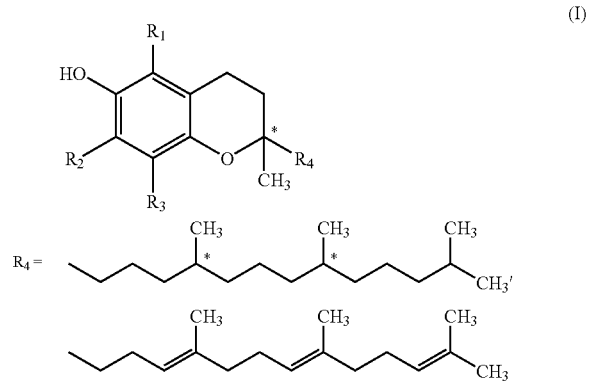

in which $R_1$, $R_2$ and $R_3$ are independently selected from the group consisting of hydrogen and $C_{1-4}$ alkyl, preferably methyl.

In the tocopherols, $R_4$ is 4:8:12 tri-methyl tridecane and the 2, 4, and 8 positions (see *) may be stereoisomers with R or S activity or racemic. In the tocotrienols, $R_4$ is 4:8:12 tri-methyl trideca-3:7:11 triene and the 2 position may be stereoisomers with R or S activity or racemic. Most preferably, the electron transfer agent is α-tocopherol or tocotrienol.

The term "phosphate derivative" refers to the acid forms of phosphorylated electron transfer agents, salts of the phosphates including metal salts such as alkali or alkaline earth metal salts for example sodium, magnesium, potassium and calcium salts and any other derivative in which the phosphate proton is replaced by other substituents such as $C_1$-$C_4$ alkyl groups or phosphatidyl groups.

In some situations, it may be necessary to use a phosphate derivative such as a phosphatide. Phosphatidyl derivatives are amino alkyl derivatives of organic phosphates. These derivatives may be prepared from amines having a structure of $R_5R_6N(CH_2)_nOH$ in which n is an integer of 1 to 6 and $R_5$ and $R_6$ are independently selected from H and $C_{1-4}$ alkyl. The phosphatidyl derivatives are prepared by displacing the hydroxyl proton of the electron transfer agent with a phosphate entity that is then reacted with an amine, such as ethanolamine or N,N' dimethylethanolamine. One method of preparing the phosphatidyl derivatives involves a basic solvent such as pyridine or triethylamine with phosphorous oxychloride to prepare an intermediate which is then reacted with the hydroxy group of the amine to produce the corresponding phosphatidyl derivative, such as P cholyl P tocopheryl dihydrogen phosphate.

The term "$C_{1-4}$ alkyl" refers to straight chain, branched chain or cyclic hydrocarbon groups having from 1 to 4 carbon atoms. Examples include methyl, ethyl, propyl, isopropyl, butyl, isobutyl, sec-butyl, tert-butyl, cyclopropyl and cyclobutyl.

Particularly preferred electron transfer agent phosphate derivatives are di-tocopheryl phosphate derivatives, di-tocopheryl di-phosphate derivatives, di-tocotrienol phosphate derivatives, mono-tocopheryl phosphate derivatives, mono-tocopheryl di-phosphate derivatives and mono-tocotrienyl phosphate derivatives, most preferably a combination of mono-tocopheryl phosphate derivatives and di-tocopheryl phosphate derivatives.

It has been found that the stability of the carrier increases as the concentration of mono-electron transfer agent such as mono-α-tocopheryl phosphate increases. When a combination of mono-α-tocopheryl phosphate and di-tocopheryl phosphate is present they are preferably in a 4:1 to 1:4 ratio, more preferably a 2:1 ratio.

The amount of electron transfer agent phosphate derivative present is preferably in the range of up to 11%, more preferably 1 to 11%, most preferably 1 to 3%.

Complex of Electron Transfer Agent Phosphate Derivative

Complexes of electron transfer agent phosphate derivatives may also be used when additional properties such as improved stability or deliverability are desirable. The complex is a reaction product of one or more electron transfer agent phosphate derivatives and one or more complexing agents selected from the group consisting of amphoteric surfactants, cationic surfactants, amino acids having nitrogen functional groups and proteins rich in these amino acids such as those disclosed in International Patent Publication No. WO 02/40034, incorporated herein by reference.

The preferred complexing agents are selected from the group consisting of amino acids such as arginine and lysine and tertiary substituted amines such as those of formula (II):

$$NR_7R_8R_9 \qquad (II)$$

in which $R_7$ is selected from the group consisting of $C_{6-22}$ alkyl optionally interrupted by carbonyl; and $R_8$ and $R_9$ are independently selected from the group consisting of H, $CH_2COOX$, $CH_2CHOHCH_2SO_3X$, $CH_2CHOHCH_2OPO_3X$, $CH_2CH_2COOX$, $CH_2COOX$, $CH_2CH_2CHOHCH_2SO_3X$ or $CH_2CH_2CHOHCH_2OPO_3X$ in which X is H, Na, K or alkanolamine, provided that $R_8$ and $R_9$ are not both H and when $R^7$ is RCO, then $R^8NCH_3$ and $R^9$ is $(CH_2CH_2)N(C_2H_4OH)$—$H_2CHOPO_3$ or $R^8$ and $R^9$ together form $N(CH_2)_2N(C_2H_4OH)CH_2COO$.

Preferred complexing agents include arginine, lysine or lauryliminodipropionic acid where complexation occurs between the alkaline nitrogen centre and the phosphoric acid ester to form a stable complex.

The term "$C_{6-22}$ alkyl" refers to straight chain, branched chain or cyclic hydrocarbon groups having from 6 to 22 carbon atoms, Examples include hexyl, cyclohexyl, decyl, dodecyl, tridecyl, tetradecyl, pentadecyl, hexadecyl, heptadecyl and octadecyl.

Biologically Active Compound

The term "biologically active compound" refers to compounds having a biological effect in humans or animals for medical, veterinary or cosmetic applications. Biologically active compounds include pharmaceuticals or derivatives thereof, in particular phosphate derivatives thereof. Pharmaceuticals include vitamins, phytochemicals, cosmetic agents, nutraceuticals, peptides, polypeptides, proteins or nucleic acids. It will be appreciated that some of the biologically active compounds can be classified in more than one of these classes.

Examples of pharmaceuticals include but are not limited to narcotic analgesics such as morphine, oxycodone, and levorphanol; moderate opioid agonists such as codeine and propoxyphene; mixed opioid agonists such as buprenorphine and pentazocine; opioid antagonists such as naloxone and naltrexone; non-opioid analgesics such as acetaminophen and phenacetin; corticosteroids such as cortisone; inhaled anaesthetics such as halothane, enflurane; intravenous anaesthetics such as barbiturates, benzodiazepines, opioids, neuroleptics (e.g. droperidol with fentanyl), ketamine and propofol; local anaesthetics such as procaine and lignocaine; antiemetics such as scopolamine; sympathomimetic pharmaceuticals such as adrenaline and dopamine; adrenergic agonists such as direct-acting agonists (e.g. dobutamine and epinephrine), indirect acting agonists (e.g. amphetamine and tyramine) and direct and indirect (mixed action) agonists (e.g. ephedrine and metaraminol), adrenergic antagonists such as alpha blockers (e.g. prazosin and phentolamine), beta blockers (e.g. atenolol, timolol and pindolol) and drugs affecting neurotransmitter uptake or release (e.g. cocaine, reserpine and guanethidine); anticholinergic pharmaceuticals such as antimuscarinic agents (e.g. atropine and atropine phosphate), ganglionic blockers (e.g. nicotine and mecamylamine), neuromuscular blockers (e.g. atracurium and tubocurarine); direct cholinergic agonists such as pilocarpine; indirect cholinergic agonists (reversible and irreversible) such as neostigmine and echothiophate; antiparkinson's pharmaceuticals such as amantadine, levodopa, tolcapone, ropinirole, selegiline and bromocriptine; hormones and fragments thereof such as sex hormones, human parathyroid hormone (PTH), growth hormone and insulin; anti-diabetic pharmaceuticals such as insulin, glucagon-like peptides and hypoglycaemic agents such as sulfonylureas, biguanides, α-glucosidase inhibitors and thaiazolidinediones; anti-anginal agents such as organic nitrates (e.g. isosorbide and nitroglycerine), ranolazine, b-blockers and calcium channel blockers (e.g. diltiazem, nifedipine and verapamil); anti-anxiety and hypnotic agents such as benzodiazepines (e.g. alprazolam and diazepam), buspirone, hydroxyzine, zolpidem, barbiturates (e.g. phenobarbital) and non-barbiturate sedatives (e.g. antihistamines and chloral hydrate); psychomotor stimulants such as amphetamine, caffeine, cocaine, theophylline and nicotine; antidepressants such as tricyclic/polycyclic antidepressants (e.g. amitriptyline), selective serotonin re-uptake inhibitors (e.g fluoxetine), monoamine oxidase inhibitors (e.g. phenelzine); neuroleptic agents such as typical antipsychotics (e.g. phenothiazines and butyrophenones such as chlorpromazine and haloperidol) and atypical antipsychotics (e.g. benzisoxazoles, dibenzodiazepines and thienobenzodiazepines such as risperidone, clozapine and olanzapine); antiepileptics such as carbamazepine, benzodiazepines, gapapentin, tiagabine, topiramate, vigabatrin, lamotrigine, ethosuximide, valproic acid, barbiturates and phenyloin; congestive heart-failure pharmaceuticals such as vasodilators, diuretics and inotropic agents (e.g. cardiac glycosides, beta-adrenergic agonists and phosphodiesterase inhibitors); vasodilators such as ACE inhibitors (e.g. enalapril), hydralazine, isosorbide and minoxidil; diuretics such as thiazide diuretics (e.g. hydrochlorothiazide), loop diuretics (e.g. frusemide), potassium sparing diuretics (e.g. amiloride) and carbonic anhydrase inhibitors (e.g. acetazolamide); cardiac glycosides such as digoxin; β-adrenergic agonists such as dobutamine; phosphodiesterase inhibitors such as amrinone and milrinone; antiarrythmic agents such as sodium channel blockers (e.g. disopyramide, flecamide, lidocaine), β-adrenoceptor blockers (e.g. metoprolol, esmolol and propranolol), potassium channel blockers (e.g. amiodarone and sotalol), calcium channel blockers (e.g. diltiazem and verapamil), adenosine and digoxin; antihypertensive agents such as diuretics (e.g. thiazides, loop diuretics and potassium sparing diuretics), beta-blockers (e.g. atenolol), ace inhibitors (e.g. enalapril and ramipril), angiotensin II antagonists (e.g losartan), calcium channel blockers (e.g. amlodipine, nifedipine and verapamil), alpha-blockers (e.g. doxasozin, prazosin and terazosin) and others such as clonidine, diazoxide and hydralazine; platelet inhibitors such as abciximab, aspirin, clopidrogel and tirofiban; anticoagulants such as enoxaprin, heparin and warfarin; thrombolytic agents such as alteplase, streptokinase and urokinase; treatments for bleeding such as aminocaproic acid, tranexamic acid and vitamin K; treatments for anaemia such as erythropoietin, iron, folic acid and cyanocobalamin; thrombin inhibitors such as lepirudin; antimicrobial agents such as agents with activity against one or more of anaerobic organisms, gram-positive organisms and gram-negative organisms; antimicrobials with broad spectrum (e.g. tetracycline and chloramphenical), narrow spectrum (e.g. isoniazid) and extended spectrum activity (e.g. ampicillin); antimicrobials which inhibit metabolism (e.g. sulfonamides and trimethoprim), inhibit cell wall synthesis (e.g. β-lactams and vancomycin), inhibit protein synthesis (e.g. teracyclines, aminoglycosides, macrolides, clindamycin and chloramphenicol) and which inhibit nucleic acid function or synthesis (e.g. fluoroquinolones and rifampicin); antimycobacterial agents such as agents used to treat tuberculosis and leprosy; antifungal agents such as amphotericin B, fluconazole, flucytosine, itraconozole, ketoconazole, clotrimazole, econazole, griseofulvin, miconazole and nystatin; antiprotozoal agents such as chloroquine, metronidazole, mefloquine, pyrimethamine, quinacrine, and quinidine; anthelmintic agents such as praziquantel, and mebendazole; antiviral agents for respiratory infections (e.g. amantadine, ribavirin and rimantadine), for herpes and cyto-megalovirus infections (e.g. acyclovir, cidofovir, penciclovir, famciclovir, ganciclovir and vidarabine), for human immunodeficiency virus infections (e.g. abacavir, adefovir, apmrenavir, delavirdine, didanosine, stavudine, zalcitabine and zidovudine) and for hepatitis, leukemia and kaposi's sarcoma (e.g. interferon); anticancer agents such as antimetabolites (e.g. cytarabine, fludarabine, 5-fluorouracil, 6-mercaptopurine, methotrexate and 6-thioguanine) and antibiotics (e.g. bleomycin, doxorubicin, daunorubicin and plicamycin), alkylating agents (e.g. carmustine, lomustine, cyclophosphamide, ifosfamide, streptozotocin and mechlorethamine), microtubule inhibitors (e.g. navelbine, paclitaxel, vinblastine and vincristine), steroid hormones and their antagonists (e.g. aminoglutethimides, estrogens, flutamide, goserelin, leuprolide, prednisone and tamoxifen) and others such as asparaginase, cisplatin, carboplatin, etoposide, interferons and procarbazine; anti-inflammatory agents such as non-steroidal anti-inflammatory drugs (e.g. aspirin, diclofenac, ibuprofen, naproxen, sulindac, piroxicam, phenylbutazone, tolmetin, indomethacin and ketoprofen), cyclooxegenase 2 inhibitors (e.g. celecoxib and rofecoxib), anti-arthritis agents (e.g. chloroquine, gold salts, methotrexate and D-penicillamine) and gout treatments (e.g. allopurinol, colchicine, probenecid and sulfinpyrazone); autacoids and autacoid antagonists such as prostaglandins (e.g. carbopost, misoprostol and dinoprost), H1 antihistamines (e.g. clyclizine, meclizine, dimenhydrinate, diphenhydramine, fexofenadine, cetirizine and loratadine), H2 antihistamines (e.g. cimetidine, famotidine, nizatadine and ranitidine) and agents used to treat migraine headaches (e.g. β-blockers, dihydroergotamine, ergotamine, methysergide and sumatriptan); asthma pharmaceuticals such as beta-adrenergic agonists, corticosteroids, prophylactic anti-inflammatory agents (e.g. cromolyn and nedocromil) and cholinergic antagonists (e.g. ipratropium); agents affecting the respiratory system such as agents that target that formation or function of leukotrienes (e.g. montelukast, zileuton and zafirlukast); allergic rhinitis pharmaceuticals such as antihistamines, alpha-adrenergic agonists, corticosteroids and prophylactic anti-inflammatory agents such as cromolyn; chronic obstructive pulmonary disease pharmaceuticals such as bronchodilators (e.g. beta-adrenergic agonists and cholinergic antagonists, xanthine-oxidase inhibitors such as theophylline) and glucocorticoids; steroid hormones and their antagonists such as estrogens (e.g. estradiol, mestranol and quinestrol), selective estrogen modulators (e.g. raloxifene), progestins (e.g. hydroxyprogesterone, norgestrel, norethindrone and medroxyprogesterone), antiprogestins (e.g. mifepristone), androgens (e.g. danazol, nandrolone, stanozolol, testosterone, testosterone cypionate and fluoxymesterone), antiandrogens (e.g. cyproterone, finasteride and flutamide), corticosteroids (e.g. beclomethasone, cortisone, dexamethasone, fludrocortisone, prednisolone and triamcinolone), and inhibitors or adrenocorticoid biosynthesis (e.g. aminoglutethimide, ketoconazole, metyrapone, mifepristone and spironolactone); osteoporosis treatments such as biphosphonates (e.g. alendronate, pamidronate and risedronate), calcitonin, calcium and estrogens; anti-obesity agents such as lipase inhibitors (e.g. orlistat), anti-obesity peptides (e.g. growth hormone and fragments thereof) and sympathomimetic agents; treatments for gastric ulcers and inflammation such as proton pump inhibitors (e.g. omeprazole and lansoprazole), antimicrobials, prostaglandins (e.g. misoprostol) and H2 antihistamines (e.g. ranitidine); antibody pharmaceuticals; antithyroid pharmaceuticals such as thyroxine; peptide, protein and polypeptide pharmaceuticals such as nucleic acids, oligonucleotides, antisense pharmaceuticals, enzymes, cytokines (e.g. tumour necrosis factor), cytokine analogues, cytokine agonists, cytokine antagonists, hormones (e.g. calcitonin, and parathyroid hormone), hormone fragments (e.g. teriparatide), hormone analogues (e.g. growth hormone agonists, growth hormone antagonists such as octreotide, and analogues of gonadotropin releasing hormone such as leuprolide), insulin, insulin fragments, insulin analogues (e.g. recombinant human insulin analogues, lispro, glargine, aspart and detemir), glucagon-like-peptide, glucagon-like-peptide fragments, glucagon-like peptide analogues (e.g. exenatide), immunoglobulins, antibodies, vaccines, gene therapies, lipoproteins, erythropoietin, enfuvirtide and eptifibatide; hormone, protein, peptide, polypeptide, nucleic acid and oligonucleotide therapies that are direct or indirect agonists, antagonists, modulators, stimulants or inhibitors of natural hormones, proteins, peptides, polypeptides, nucleic acids and oligonucleotides; small molecule and large molecule therapeutic proteins, peptides, polypeptides, nucleic acids and oligonucleotides made synthetically, by recombinant methods, or by chemical modification of a natural product; synthetic or naturally derived small molecule and large molecule therapeutic proteins, peptides, polypeptides, nucleic acids and oligonucleotides; small molecule therapeutic peptides such as growth factors, hormones, cytokines and chemokines; analogues, fragments and variants of natural proteins, peptides, polypeptides, oligonucleotides and nucleic acids and such like compounds (e.g. hematide a variant of erythropoietin and octreotide an analogue of somatostatin); hormones, proteins, peptides, polypeptides, oligonucleotides and nucleic acids for the treatment, or prevention of human and animal diseases such as allergy/asthma, arthritis, cancer, diabetes, growth impairment, cardiovascular diseases, inflammation, immunological disorders, baldness, pain, opthalmological diseases, epilepsy, gynaecological disorders, CNS diseases, viral infections, bacterial infections, GI diseases, obesity, and haemological diseases; phytochemicals such as α-bisabolol, eugenol, silybin, soy isoflavones, phytosterols and iridoid gylcosides for example aucubin and catalpol; sesquiterpene lactones such as pseudoguaianolide from Arnica chamissonis; terpenes such as rosmarinic acid and rosmanol; phenolic glycosides such as salicylates for example salicin, saligenin and salicyclic acid; triterpenes such as taxasterol, α-lactucerol, isolactucerol and taraxacoside; hydroquinone derivatives such as arbutin; phenylalkanones such as gingerols and shagaols; hypercin; antidyslipidaemic agents such as HMGCoA reductase inhibitors (e.g. simvastatin, atorvastatin and pravastatin), fibrates (e.g. clofibrate and gemfibrozil), niacin, probucol, cholesterol absorption inhibitors (e.g. ezetimibe), cholesterol ester transferase antagonists (e.g. torcetrapib), HDL cholesterol elevating agents (e.g. torcetrapib); triglyceride reducing agents (e.g. fibrates), V-protectants (e.g. AGI-1067), variants of human apolipoprotein (e.g. ETC-216); acylphloroglucides such as xanthohumol, lupulone, humulone and 2-methylbut-3-en-2-ol; nutraceuticals such as nutritional health or other supplements, vitamins for example co-enzyme Q and retinol (Vitamin A), nutrients, precursor molecules for generation of hormones, proteins for example elastin, collagen and insulin, amino acids, plant extracts such as grape seed extract, ephedrine, DHEA, isoflavones and phytosterols; and cosmetics such as anti-ageing or anti-wrinkle agents for example elastin and collagen and antioxidants such as retinol and co-enzyme Q, retinoic acid, omega-3-fatty acids, glucosamine, gamma-tocopheryl and gamma-tocopheryl phosphate derivatives.

It will be understood that the pharmaceutically acceptable salts and derivatives of the pharmaceuticals described above are included within the scope of the present invention.

Preferably, the amount of biologically active compound is in the range of up to 50, more preferably 0.5 to 30, most preferably 0.5 to 20.

Vesicles

The vesicles when present may have a diameter in the range of 50 to 10,000 nm, more preferably 100 to 500 nm, most preferably 300 to 500 nm.

The biologically active compound may be at least partially encapsulated by the vesicles.

Types of Administration

The formulations include those suitable for parenteral, enteral, oral, topical, transdermal, opthalmological, rectal, vaginal, intranasal and intrapulmonary administration. The formulations may be in the form of liquids, solutions, suspensions, creams, ointments, lotions, gels, powders, aerosols, patches, enteric coated tablets, capsules, suppositories, pessaries or tampons and prepared by any methods well known in the art of pharmacy such as described in Remington J P. The Science and Practice of Pharmacy, ed. A R Gennaro, 20$^{th}$ edition, Lippincott, Williams and Wilkins Baltimore, Md. (2000). These methods include the step of bringing into association the biologically active compound with the carrier, and then, if necessary, shaping the formulation into the desired product.

The formulation may be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants.

Formulations for parenteral use may be presented in unit dosage forms (e.g., in single dose-ampoules), or in vials containing several doses and in which a suitable preservative may be added. The formulation may be in form of a solution, a suspension, an emulsion, an infusion device, or a delivery device for implantation or it may be presented as a dry powder to be reconstituted with water or another suitable vehicle before use. Apart from the biologically active compound, the formulation may include suitable parenterally acceptable carriers and/or excipients. The biologically active compound may be incorporated into microspheres, microcapsules, nanoparticles, liposomes, or the like for controlled release. Furthermore, the formulation may include suspending, solubilizing, stabilizing, pH-adjusting agents, and/or dispersing agents.

As indicated above, the formulations may be in the form suitable for sterile injection. To prepare such a formulation, the biologically active compound is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene or glycol or the like.

Controlled release parenteral compositions may be in form of aqueous suspensions, microspheres, microcapsules, magnetic microspheres, oil solutions, oil suspensions, or emulsions. Alternatively, the biologically active compound may be incorporated in biocompatible carriers, liposomes, nanoparticles, implants, or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamine) and poly(lactic acid).

Biocompatible carriers that may be used when formulating a controlled release parenteral formulation are carbohydrates (e.g., dextrans), proteins (e.g., albumin), lipoproteins, or antibodies.

Materials for use in implants can be non-biodegradable (e.g., polydimethyl siloxane) or biodegradable (e.g., poly (caprolactone), poly(lactic acid), poly(glycolic acid) or poly (ortho esters)).

Formulations suitable for oral administration may conveniently be presented as discrete units such as capsules, cachets or tablets each containing a predetermined amount of the biologically active compound; as a powder or granules; as a solution, a suspension or as an emulsion. The biologically active compound may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may for example be in the form of aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles which may include edible oils, or preservatives.

For topical administration transdermally, the biologically active compounds may be formulated as ointments, creams or lotions, or as a transdermal patch. Ointments and creams may, for example, be formulated with an aqueous or oily base with the additional of suitable thickening and/or gelling agents. Lotions may be formulated with an aqueous or oily base, and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and gum acacia or gum tragacanth; pastilles comprising the active ingredient in an inert base such as gelatin or sucrose and gum acacia; and mouthwashes comprising the active ingredient in a suitable liquid carrier.

Formulations suitable for rectal administration may be presented as suppositories. Suitable excipients include cocoa butter and other materials commonly used in the art, and the suppositories may be conveniently formed by admixture of the biologically active compound with the softened or melted carrier(s) followed by chilling and shaping moulds.

Formulations suitable for vaginal administration may be presented as pessaries, tampons, creams, gels, pastes, foams or sprays containing in addition to the biologically active compound such excipients as are known in the art to be appropriate.

For intranasal or intrapulmonary administration, the formulations may be administered in the form of a solution or a suspension or as a dry powder.

Solutions and suspensions will generally be aqueous (for example sterile or pyrogen-free water) with a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents or surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions may be applied directly to the nasal cavity by conventional means, for example with a dropper, pipette or spray. The formulations may be provided in a single or multidose form. The latter case means of dose metering is desirably provided. In the case of a dropper or pipette this may be achieved by administering an appropriate, predetermined volume of the solution or suspension. In the case of a spray this may be achieved for example by means of metering atomising spray pump.

Administration to the respiratory tract may also be achieved by means of an aerosol formulation in which the biologically active compound is provided in a pressurised pack with a suitable propellant, such as chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of pharmaceutical may be controlled by provision of metered valve.

Alternatively the compounds may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler such as Diskhaler (Trade Mark of GlaxoSmithKline) or meter dose aerosol inhaler.

Other Excipients

A person skilled in the art would know which other excipients could be included in the formulation. The choice of other excipients will depend on the characteristics of the biologically active compound and the form of administration used. Examples of other excipients include solvents, thickeners or gelling agents, surfactants, buffers, emollients, sweeteners, disintegrators, flavours, colours, preservatives, fragrances, electrolytes, film foaming polymers and the like. Suitable sweeteners include sucrose, lactose, glucose, aspartame or saccharin. Suitable disintegrators include corn starch, methylcellulose, polyvinylpyrrolidon, xanthan gum, bentonite, alginic acid or agar. Suitable flavours include peppermint oil, oil of wintergreen, cherry, orange or raspberry flavouring. Suitable preservatives include sodium, benzoate, vitamin E, alphatocopheryl, ascorbic acid, methyl paraben, propyl paraben or sodium bisulphite.

Typical excipients for the formulation of the present invention include gelling agents such as carbomer (Carbopol) which is a carboxyvinylpolymer, preservatives such as methyl paraben, butyl paraben, ethyl paraben, propyl paraben and sodium benzoate and buffers such as sodium hydroxide. The excipients may be present in an amount up to about 5%.

Process for Preparing the Carrier or Formulation

The process for preparing the carrier involves combining the electron transfer agent phosphate derivatives or complexes thereof with the alcohol and then adding water. The formulation is then prepared by adding the biologically active compound to the carrier at any step of the process for preparing the carrier.

Generally the alcohol is heated to temperatures of 55° C. or more and the electron transfer agent phosphate derivatives are dissolved in the alcohol. If the biologically active compound is soluble in the alcohol, then this is added when the electron transfer agent phosphate derivatives and alcohols are combined and the balance of the formulation is made up of water.

The other excipients such as gelling agents, preservatives and buffers may be added during any step of the process, usually after addition of the water.

The components of the carrier and formulation may be combined using any suitable known mixing technique, such as, for example, shaking or vortexing.

DETAILED DESCRIPTION OF THE DRAWINGS

The examples will be described with reference to the accompanying drawings in which.

EXAMPLES

Various embodiments/aspects of the invention will now be described with reference to the following non-limiting examples.

Example 1

This example investigates the transdermal uptake of human parathyroid hormone (fragment 1-34) (PTH) using a formulation according to the invention.

Materials and Methods

The test formulations were prepared as follows. All percentages are w/w.

| Ingredient | TPM-01/PTH | TPM-02/PTH |
|---|---|---|
| PTH-(1-34) (American Peptide, USA) | 0.1% | 0.1% |
| A mixture of the acid forms of phosphorylated tocopheryls (TPM) containing TP:T$_2$P in a 2:1 ratio. TP refers to the monophosphate ester of α-tocopheryl and T$_2$P refers to di-tocopheryl phosphate. | 1% | 1% |
| Ethanol | — | 20% |
| Carbopol | 0.4% | 0.75% |
| methylparaben | 0.1% | 0.1% |
| Water | qs to 100% | qs to 100% |

The TPM-02/PTH formulation was a colloidal suspension which looked like milk. This indicated that vesicles had formed.

Treatment

Sprague-dawley rats (10-12 week old males) were randomly assigned to treatment groups (Groups 1 & 2, n=6) and housed in individual boxes to prevent their housemates from licking the formulation from their backs.

Treatment Groups:

Group 1-100 mg of TPM-01/PTH/200 g body weight twice daily for 24 hours.

Group 2-100 mg of TPM-02/PTH/200 g body weight twice daily for 24 hours.

Rats were anaesthetized, weighed and a region of ~5×4 cm immediately below the neck was shaved. Rats were tail bled while under anaesthesia and plasma collected to determine the level of PTH before the commencement of treatment. Beginning the following day, the appropriate dose of formulation for each rat was weighed out and massaged into the rat's skin using a gloved finger. Formulation was applied to Groups 1 and 2, twice daily (morning and evening) over 24 hours. At the completion of the treatment period, rats were killed by CO$_2$ asphyxiation and bled by heart puncture.

Analysis of PTH in plasma: Plasma was separated from the collected blood by centrifugation and stored at −20° C. until analysis. Levels of PTH in rat plasma was analysed using the Human Bioactive PTH 1-34 ELISA Kit (Immunotopics Inc., USA) as per the manufacturer's instructions.

Results

Figure 1:
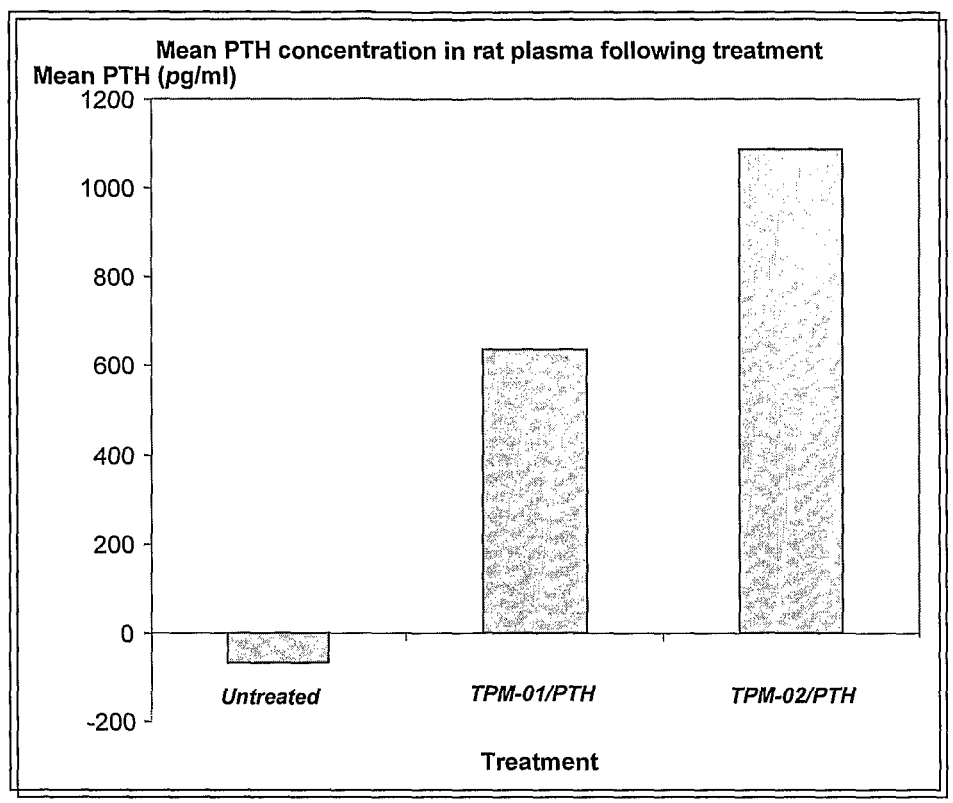
FIG. 1 is a graph showing mean PTH concentration in the rat plasma.

Mean PTH levels detected in plasma are summarized in FIG. 1.

Twice daily application of TPM-01/PTH produced a significant (p<0.05*) increase in the amount of PTH present within plasma after 24 hours. Mean plasma PTH levels were increased by 685 pg/ml relative to the basal level in the untreated rats. This increase in plasma represents 4.5% percent of the total dose.

Twice daily application of TPM-02/PTH produced a significant ($p<0.05*$) increase in the amount of PTH present within plasma after 24 hours. This increase (1185 pg/ml) represents 7.7% of the total dose, and a 70% improvement over the TPM-01/PTH formulation.

Results of Student's t-Test

Transdermal treatment with TPM-02/PTH increased the levels of PTH in rat plasma indicating that the TPM was able to enable the absorption of PTH-(1-34) across the skin over 24 hours, significantly elevating circulating PTH plasma levels compared to untreated controls. 72 hours after treatment, the plasma levels of PTH had returned to basal levels.

Reported studies show that following subcutaneous injection of therapeutic amounts (25 µg/kg body weight), PTH levels in rat plasma peak ~40-60 minutes after injection, and are completely turned over within 4 hours. Although applied topically, the rats in this study received a much larger dose (500 µg/kg body weight). Given the rapid rate of PTH turnover, it is reasonable to conclude that the high levels of PTH remaining 24 hours after the initial application represent only a small percentage of the total dose received. The effective dose produced by topical application of the TPM formulations would therefore be much larger than the levels of PTH measured after 24 hours.

Conclusions

Although both the TPM-01 and TPM-02 formulations were effective at delivering PTH, TPM-02/PTH delivered 70% more PTH to the circulatory system than TPM-01/PTH. The formulation according to the invention is more effective in delivering actives through skin and into the systemic circulation.

Example 2

This method describes the production of 100 ml of a Co-enzyme Q (CoQ)/tocopheryl phosphate mixture formulation for subsequent use in formulations according to the invention. The final formulation contains 0.5% CoQ10, 1% TPM, 10% ethanol, 1% carbopol, 0.1% methylparaben, QS MilliQ.

Equipment and Materials
Ethanol (AR grade)
MilliQ water
Co-enzyme Q (Kaneka)
Tocopheryl phosphate mixture (TPM) containing tocopheryl phosphate (TP) and di-tocopheryl phosphate (T2P), in a ratio of 2:1 w/w (Phosphagenics Ltd).
Carbomer 934P USP powder (Croda Surfactants Ltd)
Methylparaben BP powder (Bronson & Jacobs)
1M Sodium hydroxide (NaOH)
Balance (Mettler AE 240)
Falcon tube
100 ml plastic specimen container
Water bath 70° C.
Multi-Vortex Procedure
1. Weighed accurately 0.5 g of CoQ into a 50 ml Falcon tube.
2. Weighed accurately 1 g of TPM into the same 50 ml Falcon tube.
3. Weighed 10 g (not ml) ethanol into the tube. Capped tightly and mixed.
4. Heated in a 70° C. water bath to help dissolve/melt the components. Shaked by hand every few minutes until both CoQ and TPM had dissolved. Left in heat until needed. At this concentration CoQ, precipitated out of the ethanol upon cooling.
5. Measured 80 ml MilliQ into a 100 ml specimen container. Capped tightly and placed in water bath for 5 minutes to warm the water.
6. Poured the heated CoQ/TPM/ethanol solution directly into the MilliQ.
7. Capped immediately and shaked vigorously by hand to mix the components. The formulation had an opaque, yellow appearance. Vortex for 5 minutes.
8. Weighed accurately 1 g of Carbopol and 100 mg of methylparaben into a weigh boat. Added gradually to CoQ/TPM solution, with vigorous vortexing between each addition. Heated the sample in the 70° C. water bath for short periods to help the samples to dissolve.
9. Once all carbopol/methylparaben had been added, vortexed until the components achieve an even consistency, although at this stage it had not formed a gel.
10. Added 3 ml 1M NaOH, cap and shake vigorously.
11. If the formulation had not formed a gel, checked the pH. Carbopol will form an optimal gel between pH 7-8.
12. Repeated steps 10 and 11 until a gel of the desired consistency was formed.
13. If necessary, made up to 100 g with MilliQ.
14. Vortexed for a further 5 minutes.
15. Wrapped container in foil to prevent photodegradation of CoQ.
16. By the next day, any remaining lumps of undissolved carbopol will have absorbed water from the formulation and formed clear pockets of gel. Shaked vigorously until the formulation assumed an even consistency.

The formulation was a colloidal suspension which looked like milk. This indicated that the vesicles had formed.

Example 3

This example investigates the transdermal uptake of coenzyme Q10 (CoQ10) using a formulation according to the invention.

Materials and Methods
Ethanol (AR grade)
MilliQ water (in-house supply)
Tocopheryl phosphate mixture (TPM) containing tocopheryl phosphate (TP) and ditocopheryl phosphate (T2P), in a ratio of 2:1 w/w (Phosphagenics Ltd).
Co-enzyme Q (CoQ) (Kaneka, Japan)
Nivea Visage® Anti-wrinkle Q10 Day Care (Beiersdorf)
Carbomer 934P USP powder (Croda Surfactants Ltd)
Methylparaben BP powder (Bronson & Jacobs)
1M Sodium hydroxide (NaOH)
Balance (Mettler AE 240)
Falcon tube
100 ml plastic specimen container
Water bath 55° C.
Multi-Vortex Test Formulations CoQ Control:

The CoQ Control formulation was used to assess the amount of CoQ10 able to penetrate the skin in the absence of TPM. Contents: 0.5% CoQ10 (Kaneka, Japan), 10% ethanol, 1% carbopol, 0.1% methylparaben, made up to 100% with water.

Weighed 0.5 g of CoQ10 into a 50 ml Falcon tube. Added 10 g ethanol using the benchtop balance. Capped tightly and mixed. Heated in a 55° C. water bath to help dissolve/melt the CoQ. Left in heat until needed. At this concentration CoQ precipitated out of the ethanol upon cooling. Measured 80 ml of water into a 100 ml specimen container. Poured the heated CoQ/ethanol solution directly into the water. Capped immediately and shaked vigorously by hand to mix the components. Vortexed for 5 minutes. Some CoQ10 came out of solution, forming an oily orange ring around the container. This cannot be avoided due to the insoluble nature of CoQ10. Weighed accurately 1 g of Carbopol and 100 mg of methylparaben into a weigh boat. Poured into formulation and vortexed until an even consistency was achieved, although at this stage it will not have formed a gel. Added 3 ml 1M NaOH, capped and shaked vigorously. If the formulation had not formed a gel, checked the pH. Carbopol will form an optimal gel between pH 7-8. Repeated the addition of 3 ml 1M NaOH, shaked and checked pH until a gel formed. If necessary, make up to 100 g with MilliQ. Vortexed for a further 5 minutes. Wrapped container in foil to prevent photodegradation of CoQ. By the next day, any remaining lumps of undissolved carbopol will have absorbed water from the formulation and formed clear pockets of gel. Vortexed vigorously until the formulation assumed an even consistency.

TPM Control:

The TPM Control formulation was used to determine the effect of TPM on endogenous CoQ10 levels. Contents: 1% TPM, 10% ethanol, 1% carbopol, 0.1% methylparaben, made up to 100% with water. No CoQ10 is present in this formulation.

Weighed 1 g of TPM into a 50 ml Falcon tube. Added 10 g ethanol using the benchtop balance. Capped tightly and mixed. Heated in a 55° C. water bath to help dissolve/melt the TPM. Left in heat until needed. Measured 80 ml of water into a 100 ml specimen container. Poured the heated TPM/ethanol solution directly into the water. The formulation immediately gained a milky quality. Capped immediately and shaked vigorously by hand to mix the components. Vortexed for 5 minutes. Weighed accurately 1 g of Carbopol and 100 mg of methylparaben into a weigh boat. Poured into formulation and vortexed until an even consistency was achieved, although at this stage it will not have formed a gel. Added 3 ml 1M NaOH, capped and shaked vigorously. If the formulation had not formed a gel, checked the pH. Carbopol will form an optimal gel between pH 7-8. Repeated the addition of 3 ml 1M NaOH, shaked and checked pH until a gel formed. If necessary, made up to 100 g with water. Vortexed for a further 5 minutes. Wrapped container in foil to prevent photodegradation of CoQ. By the next day, any remaining lumps of undissolved carbopol will have absorbed water from the formulation and formed clear pockets of gel. Vortexed vigorously until the formulation assumed an even consistency.

TPM-02/CoQ:

The TPM-02/CoQ formulation according to the invention was prepared as set out in Example 2 above. Contents: 0.50 CoQ10, 1% TPM, 10% ethanol, 1% carbopol, 0.1% methylparaben, made up to 100% with water.

Nivea Visage® Anti-Wrinkle Q10 Day Care (Beiersdorf, Germany):

Nivea Visage® is a commercially available facial cream advertised as an effective source of CoQ10 for skin. As the exact CoQ10 content is unknown, the Nivea Visage® was compared with the TPM-02/CoQ on a weight-by-weight basis. Contents: Unknown Treatment Groups Sprague-dawley rats (10-12 week old males) were purchased from Animal Services, Monash University and acclimatised to the Departmental Animal House for a minimum of 5 days before the treatments commenced. Animals were randomly assigned to treatment groups (n=6), and housed in individual boxes to prevent their housemates from licking the formulation from their backs. Food (standard rat laboratory pellets; Barastoc, Australia) and water were provided freely.

Group 1—Untreated

Group 2—100 mg of CoQ Control/200 g body weight twice daily for 24 hours

Group 3—100 mg of TPM Control/200 g body weight twice daily for 24 hours

Group 4—100 mg of TPM-02/CoQ/200 g body weight twice daily for 24 hours

Group 5—100 mg of Nivea Visage® cream/200 g body weight twice daily for 24 hours Group 6—100 mg of CoQ Control/200 g body weight twice daily for 48 hours Group 7—100 mg of TPM Control/200 g body weight twice daily for 48 hours Group 8—100 mg of TPM-02/CoQ/200 g body weight twice daily for 48 hours Group 9—100 mg of Nivea Visage Cream®/200 g body weight twice daily for 48 hours Rats were anaesthetized, weighed and a region of ~5×4 cm immediately below the neck was shaved. Beginning the following day, the appropriate amount of formulation for each rat was weighed out and massaged into the rat's skin twice daily (morning and evening) over 24, or 48 hours, using a gloved finger. The formulation was restricted to areas of the dorsal skin that the rat was unable to reach while grooming.

Analysis of CoQ10 in Skin and Plasma:

At the completion of the treatment period rats were killed by asphyxiation using $CO_2$ gas. Blood was removed by heart puncture into heparinised collection tubes, and centrifuged for separation of plasma. The area of shaved skin was washed thoroughly with distilled water to remove any unabsorbed CoQ10 remaining on the surface, and the area excised. CoQ extraction from tissues and quantitation by HPLC were performed essentially according to the method of Aberg et al., (1992) Distribution and redox state of ubiquinones in rat and human tissues. *Arch Biochem Biophys* 295: 230-234.

Statistical Analysis:

Results are expressed as mean±SD. A Student's t-test was performed to determine whether there were significant differences in the levels of CoQ extracted from both the plasma and skin between the treatment groups.

Results

Table I—Mean CoQ10 levels in plasma and skin following treatment

| Treatment | Mean $CoQ_{10}$ in plasma (ng/ml) | | Mean $CoQ_{10}$ in skin (µg/g) | |
| --- | --- | --- | --- | --- |
| | 24 hours | 48 hours | 24 hours | 48 hours |
| Untreated | 27.67 ± 4.97 | — | 0.24 ± 0.04 | — |
| CoQ Control | 35.00 ± 6.45 | 36.33 ± 4.84 | 0.74 ± 0.20 | 1.73 ± 0.27 |
| TPM Control | 33.67 ± 7.06 | 28.33 ± 5.79 | 0.32 ± 0.02 | 0.61 ± 0.12 |
| TPM-02/CoQ | 59.33 ± 16.47 | 42.33 ± 8.80 | 6.13 ± 0.98 | 10.59 ± 4.08 |
| Nivea Visage ® | 41.33 ± 4.59 | 29.83 ± 6.18 | 0.38 ± 0.05 | 0.62 ± 0.11 |

Plasma

Twice daily application of TPM-02/CoQ to the dorsal region of rats produced a significant (p<0.05) increase in the amount of CoQ10 present within plasma (Table I). Mean plasma CoQ10 levels were increased by 114% (p<0.05) after treatment with TPM-02/CoQ relative to the endogenous CoQ10 levels seen in the Untreated controls. In contrast, the CoQ and TPM Controls were only able to elevate mean plasma CoQ10 levels by 26% and 22% respectively. Neither of the latter two increases achieved statistical significance. Importantly, TPM-02/CoQ significantly (p<0.05) elevated plasma CoQ10 levels by 70% relative to the CoQ Control formulation lacking TPM, evidence for the direct involvement of TPM with the ethanol in the transdermal uptake of CoQ10.

Nivea Visage® increased plasma CoQ10 levels by 49% relative to the Untreated Controls after a single day's treatment. However, the amounts of plasma CoQ10 produced by Nivea Visage® were significantly less (44%; p<0.05) than those produced by treatment with TPM-02/COQ.

Skin

Treatment with TPM-02/CoQ significantly (p<0.05) increased endogenous CoQ10 levels in skin by 2454% in the first 24 hours (Table I). By 48 hours this increase had risen to 4312% of endogenous levels. In contrast, the CoQ and TPM controls elevated mean skin CoQ10 levels by 208% and 33% respectively in the first 24 hours, and 621% and 154% by 48 hours. While significant (p<0.05), the magnitude of the increase following treatment with the TPM Control may seem to be of little interest. TPM-02/CoQ produced increases in mean skin CoQ10 relative to the CoQ Control of 728% and 512% after 24 and 48 hours respectively.

Mean skin CoQ10 levels were significantly (p<0.05) increased (1513%) by TPM-02/CoQ after 24 hours compared to the Nivea Visage®, which failed to significantly elevate skin CoQ10 levels above those seen in the other control formulations.

Conclusion

The TPM/ethanol formulation enhanced the solubility and subsequent absorption of CoQ10 across the skin, significantly elevating plasma and skin CoQ10 levels compared to control formulations which include a commercially available cosmetic source of CoQ10. Formulating compounds with a TPM/ethanol formulation according to the invention has enormous potential for the topical application and absorption of molecules known to have poor oral bioavailability, skin specificity or adverse side-effects that manifest during digestion.

Example 4

A formulation containing insulin was prepared as set out in the description above. The details of the formulation are as follows:

| Ingredient | TPM-02/Insulin |
| --- | --- |
| Insulin | 60 units/g of gel |
| A mixture of phosphorylated tocopheryls (TPM) containing TP:T$_2$P in a 2:1 ratio. TP refers to the monophosphate ester of α-tocopheryl and T$_2$P refers to di-tocopheryl phosphate. | 2% |
| Ethanol | 30% |
| Carbomer 934 | 1% |
| Water | qs to 100% |

Example 5

This example investigates the transdermal delivery of insulin formulated with TPM.

| FORMULATION COMPONENTS | LISPRO, human analogue of insulin (Eli Lilly)<br>Bovine Insulin (Sigma)<br>3-[$^{125}$I]iodotyrosyl A14) insulin, human recombinant (Amersham Biosciences, Code IM166, Batch B0602) ($^{125}$I-insulin)<br>TPM - mixed α-tocopheryl phosphate (TP) and di-tocopheryl phosphate (T2P; 2:1) |
| --- | --- |
| DOSAGE FORMULATION COMPONENTS | 32.5 U LISPRO per kg of body weight<br>10 U bovine insulin per kg of bodyweight<br>$^{125}$I-insulin (human recombinant; 400 nCi) per rat<br>2% TPM formulation |
| Experiments 1 to 3 | |
| ANIMAL MODEL SPECIFICATIONS | Sprague Dawley rats<br>Sex: male<br>Body weight range: 220-450 g<br>Age: 10-12 weeks |
| Experiment 4 | |
| ANIMAL MODEL | Pigs |

Four separate experiments were conducted to independently demonstrate the transdermal delivery of insulin using TPM formulations after topical administration. TPM was formulated with either bovine insulin, a fast acting insulin analog (LISPRO), or a radiolabelled human recombinant insulin. Successful transdermal delivery was assessed by increases in plasma insulin levels, the detection of subcutaneous radioactivity or decreased blood glucose levels after a glucose load.

Experiment 1: Increasing Plasma Insulin Levels

The dorsal skin region of male Sprague Dawley rats (220-300 g) was shaved under light anaesthesia (ether) the day before the experiment. While asleep, the rats were weighed in order to calculate the dose of nembutal and treatment formulation required for each rat. Rats were fasted overnight (~16 h) with free access to water.

Rats were anaesthetised the following morning and maintained under anaesthesia for the duration of the experiment. The test formulation contained 2% TPM, bovine insulin (3 U/100 μl; Sigma), ethanol (30%) and carbomer (1%) made up with water. Rats received a final insulin dose of 10 U/kg of bodyweight. The control group received the same formulation containing TPM but without insulin. Control (n=2) and TPM-Insulin formulation (n=2) were topically applied and massaged into the skin with a gloved finger. Serum was collected 1, 2, 3, 4 and 6 hours after administration.

A competition radioactive immunoassay (Linco Research Inc.) specific for bovine insulin was used to measure the amount of insulin present in the serum samples.

Experiment 2: Detecting Transdermal Absorption of Insulin Using Radioactive Probes.

Sprague Dawley rats (300-450 g) were prepared for the topical administration of formulations as per Experiment 1. Rats were fasted overnight (~16 h) with free access to water.

Human recombinant insulin containing a radiolabel ($^{125}$I-Insulin, Amersham Biosciences) was formulated with 2% TPM, 30% ethanol, 1% carbomer and water to form a gel (TPM-$^{125}$I-Insulin). TPM-$^{125}$I-Insulin was applied topically (as above) at a dose of ~400 nCi per rat (n=4). Control rats (n=5) received a formulation without TPM, in order to address the role of TPM in transdermal absorption. Rats were housed individually after application with free access to food and water. After 5 hours, the rats were sacrificed and the organs removed, weighed and placed in scintillation vials to determine the total amount of radioactivity in each organ. The skin was washed to remove any unabsorbed $I^{125}$-insulin remaining on the skin surface.

Experiment 3: Lowing Blood Glucose Using Transdermal Insulin

Sprague Dawley rats (220-300 g) were prepared for the topical administration of formulations as per Experiment 1. Rats were fasted overnight (~16 h) with free access to water.

The fast acting human insulin analogue, LISPRO (Eli Lilly), was formulated with 2% TPM, 30% ethanol, 1% carbomer and water to form a gel (TPM-LISPRO). The treatment group (n=15) received a topical application of TPM-LISPRO (dose of 32.5 U LISPRO/kg body weight) 30 minutes prior to the glucose load to allow the LISPRO time to enter systemic circulation. The control group (n=15) received a formulation without LISPRO. Glucose (30% w/v) was injected IP at a dose of 2 g/kg body weight (2 ml per 300 g rat).

Figure 3:
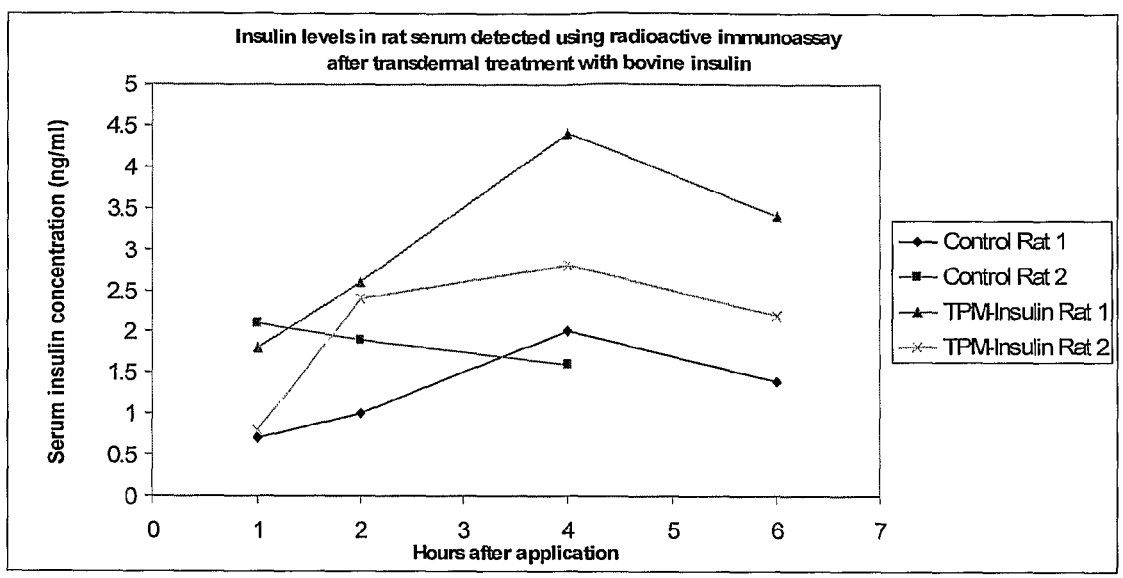
FIG. 3 is a graph of insulin levels in rat serum.

Rats were maintained under anaesthesia (nembutal) throughout the experiment, and blood glucose was measured from the tail using a Medisense Optium Blood Glucose Monitor (Abbott). The blood glucose level was measured 5 minutes after glucose load, and another 5 minutes later. Blood glucose was then measured every 10 minutes for ~2-2.5 hours. The blood glucose levels measured immediately before glucose load were subtracted from all subsequent values to determine the change in blood glucose for each rat during the experiment. The average change in blood glucose was calculated for each time point and plotted (FIG. 3). As non-diabetic rats were used in this study, the efficacy of TPM-LISPRO was judged as a reduction in peak blood glucose relative to control animals.

The area under the curve was calculated for individual rats and the population groups were compared using the Student's t-test.

Experiment 4: Lowering Blood Glucose Using Transdermal Insulin

Eight pigs with two surgically prepared catheters were prepared at least 5 days before the study. Pigs were trained to consume their feed at approximately 3:00 pm in the afternoon so that they were acclimatised to an overnight fast. The experimental design was a single reversal with the two treatments being the TPM-02 gel containing insulin or the TPM-02 gel without insulin. Intravenous (IV) infusions were separated by at least 1 day. On the day of an infusion pigs were bled every 15 min for 1 hour to obtain basal blood glucose concentrations before application of the gels. After 30 min an infusion of glucose (0.33 g/kg per h) and xylazine (0.033 mg/kg per h) was commenced and blood sampling continued for another 3 h. Blood was immediately analysed for glucose using a Glucometer. During the course of the study the catheters in one pig lost patency and so only 7 pigs entered the study. Also, on one bleed day (insulin treatment) the sampling catheter in one pig lost patency during the infusion. Therefore, the number of bleed days for the control and insulin treated pigs was 7 and 6, respectively.

Blood glucose data was analysed using REML with the fixed effects including treatment (control or insulin) and time of blood sampling while the random model included pig and bleed day. In addition, blood glucose were averaged over the pre-treatment period and over both the last 2 and 4 samples. These data were also analysed using REML with the fixed effects being bleed time (either before or after application of gel and infusion) while the random model included pig and bleed day. For these latter analyses the data were subject to log-transformation.

Results and Discussion

Pilot Experiment 1: Increasing Plasma Insulin Levels

In a trial experiment, topical application of TPM-insulin was able to increase the blood sera levels of insulin (FIG. 3). In both treated animals the increase in sera insulin levels peaked 4 hours after treatment. Insulin levels in control animals declined over this period or failed to reach similar levels as the treated animals. The small number of animals used in this pilot experiment means that statistical evaluation is not possible; however a positive trend for successful transdermal absorption is apparent, warranting further examination in larger experiments.

Figure 2:
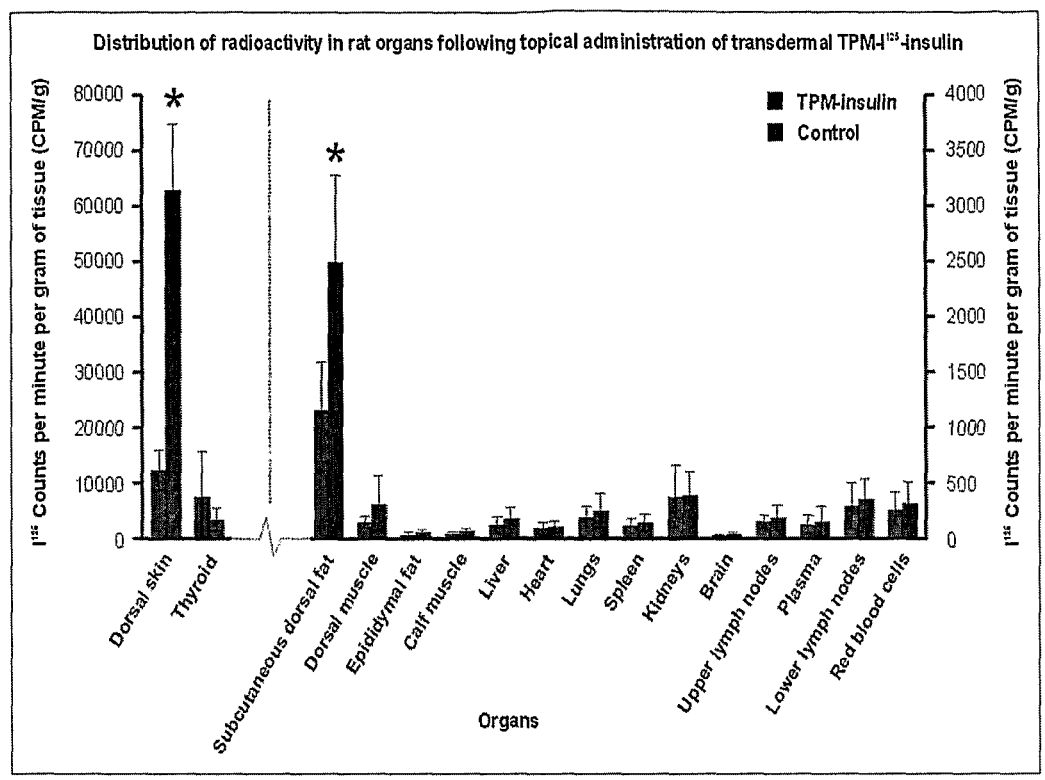
FIG. 2 is a graph showing the distribution of radioactivity in rat organs following topical administration of transdermal TPM-I$^{125}$-Insulin.

Experiment 2: Detecting Transdermal Absorption of Insulin Using Radioactive Probes Having obtained positive evidence of increased sera insulin levels in a trial experiment, we sought to conclusively demonstrate the transdermal absorption of insulin formulated with TPM. To do this, we formulated TPM with a radiolabelled form of insulin, with the aim of using its radioactive decay to monitor the transdermal absorption of "hot" insulin and subsequent distribution (if any) throughout the rat. Results show that TPM was able to successfully drive the transdermal absorption of $^{125}$I-insulin (FIG. 2). Levels of radioactivity detected within the skin at the site of application were significantly elevated (p<0.001) in comparison to control animals. As the skin surface of each rat was washed, this radioactivity is present within the deeper skin layers. Importantly, subcutaneous fat directly below the area of application contained significantly (p<0.05) increased levels of radioactivity compared to controls, conclusively demonstrating the ability of TPM to drive the absorption of insulin across the skin to the underlying tissue.

Example 3

Lowering Blood Glucose Using Transdermal Insulin

Figure 4:
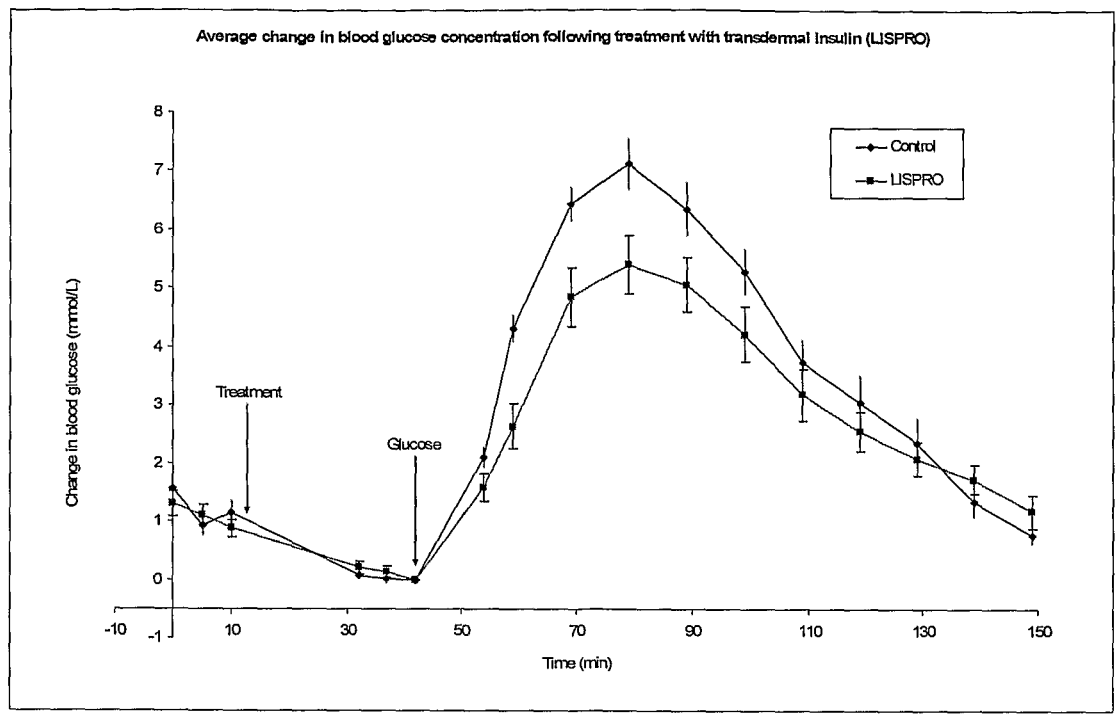
FIG. 4 is a graph of the average change in blood glucose concentration following treatment with transdermal insulin (Lispro).

Having demonstrated the successful transdermal absorption of insulin when formulated with TPM, we sought to examine whether the delivered molecule could effectively enter systemic circulation to lower blood glucose. Fasted rats were subjected to a glucose tolerance test 30 minutes after topical application of TPM-LISPRO, and blood glucose measured at subsequent intervals (FIG. 4). Blood glucose levels were significantly (p<0.02) reduced in animals treated with TPM-LISPRO compared to controls, demonstrating both the transdermal delivery, and subsequent activity of the transported LISPRO. TPM is therefore able to transport large, active molecules such as insulin across the skin.

Experiment 4: Lowering Blood Glucose Using Transdermal Insulin

This study expanded on the rat study in which glucose tolerance tests showed that the transdermal insulin formulation penetrates the skin and is bioavailable. This was assessed in pigs with an IV glucose tolerance test using TPM-02/Insulin.

Methods were refined by replacing the initial oral glucose tests that did not work as anticipated, with an IV dosing of glucose. In addition, xylazine (a chemical that inhibits insulin being released in pancreas) was co-infused with glucose.

The overall statistical effect of TPM-02/Insulin was highly significant (p<0.005). The most obvious effect appeared to be over the latter part of the infusion when blood glucose had reached plateau. At plateau, the increase in blood glucose was significantly lower in the pigs receiving the transdermal insulin preparation which represents a marked improvement in control of glycemia. The data indicate that insulin was absorbed transdermally.

The simultaneous infusion of glucose and an inhibitor of insulin secretion such as xylazine appears to be a good model system to measure transdermal delivery of insulin. Further work should extend the use of the current model to look at the effect of transdermal delivery during a more abrupt increase in blood glucose, and should extend the study time to determine for how long the delivery could be sustained. Further studies could also be conducted on a model system suitable for the target (ie. the diabetic human) such as the streptozotocin diabetic pig. That is, pigs that have been treated with the chemical streptozotocin, which destroys the insulin-secreting cells of the pancreas rendering the pig diabetic.

Conclusions:

The results presented demonstrate that mixed tocopheryl phosphates (TPM) can successfully drive the transdermal absorption of large molecules such as insulin. Increased insulin levels were demonstrated within the dermis at the site of application, the subcutaneous fat below and within the blood. Importantly, glucose tolerance tests indicate that the delivered molecule is active and able to effectively lower blood glucose. This is a positive finding for diabetics, offering hope that a non-invasive insulin delivery method may become available to alleviate the discomfort of daily injections.

It is proposed to conduct experiments using vertical diffusion (Franz) cells, with skin from pig and human, to test the flux rates and permeability of multiple variants of the formulation. This technique will allow faster optimisation of the TPM-insulin formulation.

Example 6

A formulation containing atropine was prepared as set out in the description above. The details of the formulation are as follows

| Ingredient | TPM-02/atropine |
| --- | --- |
| Atropine phosphate | 1% |
| A mixture of phosphorylated tocopheryls (TPM) containing TP:$T_2$P in a 2:1 ratio. TP refers to the monophosphate ester of α-tocopheryl and $T_2$P refers to di-tocopheryl phosphate. | 2% |
| Ethanol | 30% |
| Carbomer 934 | 1% |
| Water | qs to 100% |

Example 7

TPM vesicles containing a mixture of the monophosphate ester of α-tocopheryl (TP) and di-tocopheryl phosphate ($T_2$P) in a 2: ratio were exposed to simulated gastric and intestinal juices so as to determine whether enteric formulations of the present invention could withstand the conditions of the gut.

Vesicles were prepared with 2% TPM including the fluorescent dye Rhodamine 6G, and an analysis of the distribution of the vesicle population was done with fluorescence activated cell sorting (FACS).

Simulated gastric and intestinal juices were prepared according to the US Pharmacopoeia. Gastric juice was an acidic solution of pepsin enzyme, at pH 1.2. Intestinal juice was prepared with pancreatin powder made up in a phosphate buffer at pH 6.8.

The vesicles were exposed to both juices separately. Exposure to the simulated gastric juice created larger vesicles and/or aggregates of vesicles. Exposure to the simulated intestinal juice had almost no effect on the appearance of the vesicles, and they maintained the original size distribution.

Example 8

A formulation containing was prepared from complexes of TPM as set out in the description above to examine if complexes of TPM will form vesicles. The details of the formulation are as follows:

| Ingredient | % w/w |
| --- | --- |
| Lauryliminodiproprionic acid tocopheryl phosphate mixture (TPM) containing TP:$T_2$P in a 2:1 ratio. TP refers to the monophosphate ester of α-tocopheryl and $T_2$P refers to di-tocopheryl phosphate. | 3.2% |
| Ethanol | 30% |
| Water | qs to 100% |

Vesicles were formed according to this formulation.

The word 'comprising' and forms of the word 'comprising' as used in this description does not limit the invention claimed to exclude any variants or additions.

Modifications and improvements to the invention will be readily apparent to those skilled in the art. Such modifications and improvements are intended to be within the scope of this invention.

The invention claimed is:

1. A carrier for administering biologically active compounds comprising one or more $C_1$-$C_4$ alcohols in an amount of 5 to 40%, water in an amount of 50 to 99%, and a combination of one or more di-(electron transfer agent) phosphate compounds and one or more mono-(electron transfer agent) phosphate compounds in an amount of up to 11%, wherein the di-(electron transfer agent) phosphate compounds and the mono-(electron transfer agent) phosphate compounds are in the acid forms, and wherein the carrier is in the form of vesicles.

2. A carrier according to claim 1 in which the $C_1$-$C_4$ alcohol is selected from the group consisting of methanol, ethanol, propanol, isopropanol, butanol, and combinations thereof.

3. A carrier according to claim 2 in which the $C_1$-$C_4$ alcohol is ethanol.

4. A carrier according to claim 1 in which the $C_1$-$C_4$ alcohol is present in an amount of 10 to 30w/w %.

5. A carrier according to claim 1 in which the di- and/or mono-(electron transfer agent) phosphate compound is selected from the group consisting of hydroxy chroman phosphate compounds, phosphate compounds of quinols being the reduced forms of vitamin K1 and ubiquinone, hydroxy carotenoid phosphate compounds, calciferol phosphate compounds, and ascorbic acid phosphate compounds.

6. A carrier according to claim 5 in which the hydroxy chroman phosphate compounds are selected from the group consisting of alpha, beta, gamma and delta tocol phosphate compounds in enantiomeric and racemic forms.

7. A carrier according to claim 6 in which the tocol phosphate compound is a tocopheryl phosphate compound or a tocotrienol phosphate compound.

8. A carrier according to claim 7 in which the tocol phosphate compound is selected from the group consisting of di-tocopheryl phosphate compounds, di-tocopheryl di-phosphate compounds, di-tocotrienol phosphate compounds, mono-tocopheryl phosphate compounds, mono-tocopheryl di-phosphate compounds, and mono-tocotrienyl phosphate compounds.

9. A carrier according to claim 8 in which the tocol phosphate compound is a di-tocopheryl phosphate compound.

10. A carrier according to claim 1 in which the combination is a combination of a di-tocopheryl phosphate compound and a mono-tocopheryl phosphate compound.

11. A carrier according to claim 10 in which the w:w % ratio of mono-tocopheryl phosphate compound to di-tocopheryl phosphate compound is from 4:1 to 1:4.

12. A carrier according to claim 1 in which the combination of one or more di-(electron transfer agent) phosphate compounds and one or more mono-(electron transfer agent) phosphate compounds is present in an amount of 1 to 11w/w %.

13. A carrier according to claim 1 in which water is in an amount of 60 to 95w/w %.

14. A carrier according to claim 1 in which the vesicles have a diameter of 50 to 10,000 nm.

15. A carrier according to claim 1 in which the vesicles partially or fully encapsulate the biologically active compound.

16. A process for the preparation of the carrier as defined in claim 1 which comprises the steps of:
 (a) combining the combination of one or more di-(electron transfer agent) phosphate compounds and one or more mono-(electron transfer agent) phosphate compounds with the one or more $C_{1-4}$ alcohols; and
 (b) adding water to the combination of step (a).

17. A formulation comprising a biologically active compound and a carrier, wherein the carrier comprises one or more $C_1$-$C_4$ alcohols in an amount of 5 to 40%, water in an amount of 50 to 99%, and a combination of one or more di-(electron transfer agent) phosphate compounds and one or more mono-(electron transfer agent) phosphate compounds in an amount of up to 11%, wherein the di-(electron transfer agent) phosphate compounds and the mono-(electron transfer agent) phosphate compounds are in the acid forms.

18. A formulation according to claim 17 in which the biologically active compound is a pharmaceutical or a phosphorylated pharmaceutical.

19. A formulation according to claim 18 in which the pharmaceutical is selected from the group consisting of vitamins, phytochemicals, cosmetic agents, nutraceuticals, nutritional health or other supplements, hormones, peptides, polypeptides, proteins, amino acids, enzymes, nucleic acids, oligonucleotides, immunoglobulins, antibodies, vaccines, gene therapies, antioxidants, antimicrobial agents, antifungal agents, antiviral agents, anti herpes agents, and antibiotics.

20. A formulation according to claim 19 in which the pharmaceutical is selected from the group consisting of neuroleptic agents, narcotic analgesic agents, anti-inflammatory agents, non-steroidal anti-inflammatory agents, anti-arthritis agents, anti-obesity agents, anti-obesity peptides, lipoproteins, lipase inhibitors, vasodilators, corticosteroids, progestins, androgens, antiandrogens, anti-cancer agents, antihistamines, anti-angina agents, agents affecting the respiratory system, an allergic rhinitis pharmaceuticals, treatments for bleeding, antidyslipidaemic agents, anti-diabetic agents, insulin, hypoglycaemic agents, glucagon-like peptides, steroid hormones, growth hormones, growth hormone agonists, steroid hormone antagonists, growth hormone antagonists, octreotide, gonadotropin releasing hormones, leuprolide, human parathyroid hormone (PTH), human apolipoprotein, β-blockers, calcium channel blockers, anti-anxiety and hypnotic agents, non-barbituate sedatives, psychomotor stimulants, antidepressants, antiepileptics, cyclooxygenase 2 (COX2) inhibitors, opioid agonists, opioid antagonists, non-opioid analgesics, corticosteroids, anaesthetics, benzodiazepines, opioids, and anti-aging, anti-acne or anti-wrinkle agents.

21. A formulation according to claim 19 in which the pharmaceutical is selected from the group consisting of co-enzyme Q, human parathyroid hormone, insulin, glucagon-like peptide, morphine, oxycodone, diclofenac, lidocaine, propofol, timolol, acyclovir, clindamycin, tranexamic acid, vitamin K, folic acid, erythropoietin, iron, elastin, niacin, prostaglandins, nicotine, collagen, omega-3-fatty acids, glucosamine, grape seed extract, isoflavones and phytosterols, hydroquinone derivatives, retinol, and retinoic acid.

22. A formulation according to claim 20 in which the biologically active compound is present in an amount of up to 5w/w %.

23. A formulation according to claim 17 which further comprises one or more excipients.

24. A formulation according to claim 23 in which the excipients are selected from the group consisting of solvents, thickeners or gelling agents, surfactants, buffers, emollients, sweeteners, disintegrators, flavours, colours, preservatives, fragrances, electrolytes, and film foaming polymers.

25. A formulation according to claim 23 in which the excipients are present in an amount of up to 5w/w %.

26. A method for preparing the formulation as defined in claim 17 comprising the step of combining a biologically active compound with the carrier comprising one or more $C_1$-$C_4$ alcohols, water, and the combination of one or more di-(electron transfer agent) phosphate compounds and one or more mono-(electron transfer agent) phosphate compounds.

27. A carrier according to claim 1 in which the $C_1$-$C_4$ alcohol is a polyol of a $C_1$-$C_4$ alcohol or a polymer of a $C_1$-$C_4$ alcohol.

28. A carrier according to claim 27 in which the polyol of a $C_1$-$C_4$ alcohol is a glycol, propylene glycol, polyethylene glycol or combinations thereof.

29. A formulation according to claim 17 in which the biologically active compound and carrier are formulated for parenteral, enteral, oral, topical, transdermal, ophthalmological, rectal, vaginal, intranasal, or intrapulmonary administration.

30. A formulation according to claim 17 in which the $C_1$-$C_4$ alcohol is selected from the group consisting of methanol, ethanol, propanol, isopropanol, butanol, and combinations thereof.

31. A formulation according to claim 30 in which the $C_1$-$C_4$ alcohol is ethanol.

32. A formulation according to claim 17 in which the $C_1$-$C_4$ alcohol is a polyol of a $C_1$-$C_4$ alcohol or a polymer of a $C_1$-$C_4$ alcohol.

33. A formulation according to claim 32 in which the polyol of a $C_1$-$C_4$ alcohol is a glycol, propylene glycol, polyethylene glycol, or combinations thereof.

34. A formulation according to claim 17 in which the $C_1$-$C_4$ alcohol is present in an amount of 10 to 30w/w %.

35. A formulation according to claim 17 in which the di- and/or mono-(electron transfer agent) phosphate compound is selected from the group consisting of hydroxy chroman phosphate compounds, phosphate compounds of quinols being the reduced forms of vitamin K1 and ubiquinone, hydroxy carotenoid phosphate compounds, calciferol phosphate compounds, and ascorbic acid phosphate compounds.

36. A formulation according to claim 35 in which the hydroxy chroman phosphate compounds are selected from the group consisting of alpha, beta, gamma, and delta tocol phosphate compounds, in enantiomeric and racemic forms.

37. A formulation according to claim 36 in which the tocol phosphate compound is a tocopheryl phosphate compound or a tocotrienol phosphate compound.

38. A formulation according to claim 37 in which the tocol phosphate compound is selected from the group consisting of di-tocopheryl phosphate compounds, di-tocopheryl di-phosphate compounds, di-tocotrienol phosphate compounds, mono-tocopheryl phosphate compounds, mono-tocopheryl di-phosphate compounds, and mono-tocotrienyl phosphate compounds.

39. A formulation according to claim 38 in which the tocol phosphate compound is a di-tocopheryl phosphate compound.

40. A formulation according to claim 17 in which the combination is a combination of a di-tocopheryl phosphate compound and a mono-tocopheryl phosphate compound.

41. A formulation according to claim 10 in which the w:w % ratio of mono-tocopheryl phosphate compound to di-tocopheryl phosphate compound is from 4:1 to 1:4.

42. A formulation according to claim 17 in which water is in an amount of 60 to 95w/w %.

43. A formulation according to claim 17 in which the carrier is in the form of vesicles.

44. A formulation according to claim 43 in which the vesicles have a diameter of 50 to 10,000 nm.

45. A formulation according to claim 43 in which the vesicles partially or fully encapsulate the biologically active compound.

46. A carrier according to claim 10 in which the w:w % ratio of mono-tocopheryl phosphate compound to di-tocopheryl phosphate compound is 2:1.

47. A carrier according to claim 1 in which the combination of one or more di-(electron transfer agent) phosphate compounds and one or more mono-(electron transfer agent) phosphate compounds is present in an amount of 1 to 3w/w %.

48. A carrier according to claim 1 in which water is in an amount of 70 to 90w/w %.

49. A carrier according to claim 1 in which the vesicles have a diameter of 100 to 500 nm.

50. A carrier according to claim 1 in which the vesicles have a diameter of 300 to 500 nm.

51. A formulation according to claim 20 in which the biologically active compound is present in an amount of 0.5 to 3w/w %.

52. A formulation according to claim 20 in which the biologically active compound is present in an amount of 0.5 to 2w/w %.

53. A formulation according to claim 40 in which the w:w % ratio of mono-tocopheryl phosphate compound to di-tocopheryl phosphate compound is 2:1.

54. A formulation according to claim 17 in which water is in an amount of 70 to 90w/w %.

55. A formulation according to claim 43 in which the vesicles have a diameter of 100 to 500 nm.

56. A formulation according to claim 43 in which the vesicles have a diameter of 300 to 500 nm.

* * * * *